United States Patent
Bernuetz

(10) Patent No.: US 9,635,817 B2
(45) Date of Patent: May 2, 2017

(54) ARGYRANTHEMUM INTERGENERIC HYBRID PLANTS AND METHODS OF PRODUCTION

(75) Inventor: Andrew Bernuetz, Silverdale (AU)

(73) Assignee: BONZA BOTANICALS PTY LTD, Yellow Rock, NSW (AU)

( * ) Notice: Subject to any disclaimer, the term of this patent is extended or adjusted under 35 U.S.C. 154(b) by 1025 days.

(21) Appl. No.: 13/557,448

(22) Filed: Jul. 25, 2012

(65) Prior Publication Data

US 2012/0304334 A1   Nov. 29, 2012

Related U.S. Application Data

(63) Continuation-in-part of application No. 13/014,443, filed on Jan. 26, 2011, now Pat. No. 8,344,229.

(51) Int. Cl.
*A01H 5/02* (2006.01)

(52) U.S. Cl.
CPC .................................... *A01H 5/025* (2013.01)

(58) Field of Classification Search
None
See application file for complete search history.

(56) References Cited

U.S. PATENT DOCUMENTS

| 8,344,229 B2 | 1/2013 | Bernuetz |
| 2012/0192307 A1 | 7/2012 | Bernuetz |

FOREIGN PATENT DOCUMENTS

| AU | 2011213710 | 8/2012 |
| AU | 2011213710 | 9/2014 |
| AU | 2013204373 | 9/2014 |
| AU | 2013204373 | 1/2015 |
| JP | 2011-209666 | 8/2012 |
| JP | 2013-126887 | 9/2015 |

OTHER PUBLICATIONS

Brochmann et al (2000) Plant Systematics and Evolution 220: 77-92.*
Francisco-Ortega et al (1995) American Journal of Botany 82(10): 1321-1328.*
SiYu et al 2010, Scientia Agricultura Sinica vol. 43 No. 12, pp. 2500-2507 (Abstract only).*
Oberprieler et al 2007, Willdenowia vol. 37, pp. 89-114.*
Allard, R. W., "Principles of Plant Breeding", Second Edition, John Wiley and Sons, 1999.
Petit, T. L., and Callaway, D. J., edited by Callaway, D. J. and Callaway, B. M., "Breeding Daylilies", Breeding Ornamental Plants, Chapter 3, Timber Press, Inc., 2000, pp. 54 and 65.
Meerow, A. W., edited by Callaway, D. J. and Callaway, B. M., "Breeding Amaryllis", Breeding Ornamental Plants, Chapter 10, Timber Press, Inc., 2000, p. 191.
Cunneen, T. M., The Marguerite Daisy (*Argyranthemum* spp.): Developing an Understanding for Breeding Ph.D. dissertation, University of Sydney, 1996, pp. 4-6.
Fjellheim, S., et al., "A molecular study of hybridization and homoploid hybrid speciation in *Argyranthemum* (Asteraceae) on Tenerife, the Canary Islands", *Botanical Journal of the Linnean Society*, 2009, 159: pp. 19-31.
Forkmann, G., "Flavonoids as Flower Pigments: The Formation of the Natural Spectrum and its Extension by Genetic Engineering", *Plant Breeding*, 1999, 106: pp. 1-26.
Francisco-Ortega, J., et al., "Genetic resource conservation of the endemic genus *Argyranthemum* Sch. Bip. (Asteraceae: Anthemideae) in the Marcaronesian Islands", *Genetic Resources and Crop Evolution*, 1996, 43: pp. 33-39.
Hamrick, Debbie, Ed., "Ball Redbook", vol. 2 Crop Production, $17^{th}$ Edition, 2003, pp. 242-244.
Humphries, C. J., A Revision of the Macaronesian Genus *Argyranthemum* Webb Ex Schultz BIP. (Compositae-Anthemideae), British Museum (Natural History), 1976, pp. 147-240.
Iwazaki, Y., Ueda, Y., and Yamada, H., "Studies on the acquisition method of an intergeneric hybridization of *Argyranthemum* and *Ismelia carinata* by ovule culture", Journal of Horticulture Supplement, Society of Horticultural Research Presentations, 2007, 76(1): p. 212, (Japanese and English translations).
Mabberley, D.J., "Mabberley's Plant-Book, A portable dictionary of plants, their classifications and uses", Third Edition, Cambridge University Press, 2008, pp. 361, 436-437.
Murashige, T. and Skoog, F., "A Revised Medium for Rapid Growth and Bio Assays with Tobacco Tissue Cultures", Physiologia Plantarum, 1962, 15: pp. 473-497.
Otsuka, H., and Inaba, Z., "Breeding of *Argyranthemum* by interspecific and intergeneric hybridization. Intergeneric hybridization of *Argyranthemum* and *Ismeria carinata* (syn. *Chrysanthemum carinatum*), *I. coronaria* (syn. *Chrysanthemum coronaria*) through Ovule Culture", Journal of Horticulture Supplement, Society of Horticultural Research Presentations 2003, 72(1): p. 264 (Japanese and English translations).
Otsuka, H. and Inaba, Z., Intergeneric hybridization of marguerite (*Argyranthemum frutescens*) with annual chrysanthemum (*Glebionis carinatum*) and crown daisy (*G. coronaria*) using ovule culture, *Plant Biotechnology*, 2008, 25: pp. 535-539.
Poehlman, J. M., "Breeding Field Crops", University of Missouri, Holt, Rinehart and Winston, Inc., New York, 1966, 14 pgs.

(Continued)

*Primary Examiner* — David H Kruse
(74) *Attorney, Agent, or Firm* — Wenderoth, Lind & Ponack, L.L.P.

(57) ABSTRACT

New plants were created from a new and efficient method of intergeneric hybridization between a plant from the group *I. versicolor* and *Glebionis* sp. as a female parent and a plant from the genus *Argyranthemum* as a male parent. The plants were created by rescuing an embryo from the cross-pollination of a plant from the group *I. versicolor* and *Glebionis* sp. as a female parent with an *Argyranthemum* male parent. The invention also describes a method for infecting hybrid plants with a virus and a viroid to modify plant phenotype. In addition to providing the intergeneric hybrid plants and parts thereof, the invention provides methods for making such plants and methods for creating other intergeneric hybrid plants and self plants from normally self-incompatible plants.

22 Claims, No Drawings

(56) References Cited

OTHER PUBLICATIONS

Rose, J.B., Kubba, J. and Tobutt K.R., "Induction of Tetraploids for Breeding Hardy Ornamentals", ISHS Acta Horticulturae 560: IV International Symposium on In Vitro Culture and Horticultural Breeding, 2001, pp. 109-112.
Simmonds, N. W., "Principles of crop improvement", Longman Group Limited Essex, United Kingdon, 1979.
Takamura, T., et al., "Breeding of the Tetrapolid Yellow-Flowered Cyclamen with "EYE"", ISHS Acta Horticulturae 454: III International Symposium on New Floricultural Crops, 1998, pp. 119-126.
Van Tuyl, J. M. and van Holsteijn H.C.M., "Lily Breeding Research in the Netherlands", ISHS Acta Horticulturae 414: International Symposium on the Genus Lilium, 1996, pp. 35-45.
Watts, Leslie, "Flower and Vegetable Plant Breeding", Grower Books, London, 1980, pp. 166 and 168.
Dowrick, G. J. and El Bayoumi, A. S. "Nucleic acid content and Chromosome morphology in *Chrysanthemum*", Genet. Res. Camb., 1969, pp. 241-250, vol. 13, Great Britain.
Chaudhuri, B. K. et al., "Cytogenetics of a Cross between two Species of Annual *Chrysanthemum*", Cytologia, 1976, pp. 111-121, vol. 41.
Cunneen, T. M., "The Marguerite Daisy (*Argyranthemum* spp.): Developing an Understanding for Breeding", Ph.D. dissertation, Faculty of Agriculture, University of Sydney, 1996, pp. 10-18, Australia.
Cunneen, T. M., Breeding for Improvement of the Marguerite Daisy (*Argyranthemum* spp.), Acta Horticulturae, Ornamental Plant Improvement, 1995, pp. 101-103, vol. 420.
Dowrick, G. J., "The Chromosomes of *Chrysanthemum*, I: The Species", Heredity, 1952, pp. 365-375, vol. 6.
Brochmann, C. et al., "Multiple diploid hybrid speciation of the Canary Island endemic *Argyranthemum sundingii* (Asteraceae)", *Plant Systematics and Evolution*, 2000, pp. 77-92, vol. 20, Austria.
Boase, M.R. et al., "Chrysanthemum Systematics, Genetics, and Breeding", *Plant Breeding Reviews*, 1997, pp. 321-361, vol. 14.
Brochmann et al., Multiple diploid hybrid speciation of the Canary Island endemic Argyranthemum sundingii (Asteraceae), Plant Syst. Evol., 2000, 220:77-92.
Francisco-Ortega et al, Genetic divergence among mediterranean and macaronesian genera of the subtribe Chrystheminae(Asteraceae), Amer. J of Botany, 1995, 82(10):1321-1328.

* cited by examiner

ARGYRANTHEMUM INTERGENERIC HYBRID PLANTS AND METHODS OF PRODUCTION This application is a continuation-in-part application of prior U.S. application Ser. No. 13/014,443 filed on Jan. 26, 2011, which is incorporated by reference herein in its entirety.

BACKGROUND OF THE INVENTION

The present invention relates to *Argyranthemum* intergeneric hybrid plants and methods for increased efficiency of making hybrid plants. More specifically, the present invention relates to the production of tetraploid and aneu-tetraploid *Argyranthemum* plants and the production of intergeneric hybrid plants derived from crossing *Argyranthemum* tetraploid or aneu-tetraploid plants with plants from the group *Ismelia versicolor* and *Glebionis* sp. All publications cited are hereby incorporated by reference.

A characteristic of certain plants is the ability to occasionally cross with other species, called interspecific hybridization. Interspecific hybridization has been identified in a number of species, including *Argyranthemum*. For example, in *Argyranthemum* it has been reported that many species inter-cross naturally when geographical barriers to pollination are removed (Francisco-Ortega, J., Santos-Guerra, A., Mesa-Coello, R., Gonzalez-Feria, E., and Crawford, D., *Genetic resource conservation of the endemic genus Argyranthamum Sch. Bip. (Asteraceae: Anthimideae) in the Macronesian Islands*, Genetic Resources and Crop Evolution, 43: 33-39 (1996)). It has been suggested that with the wide range of flower colors available in commercially bred varieties of *Argyranthemum* that several species of *Argyranthemum* were involved in the development of modern cultivars, reported by Cunneen, T. M., *The Marguerite Daisy (Argyranthemum spp): developing an understanding for breeding*, Ph.D. Thesis, University of Sydney Faculty of Agriculture (1996). Thus, modern cultivars are best described as *Argyranthemum×hybrida*. All *Argyranthemum* species have a diploid chromosome number of 2n=2x=18, as reported in Humphries, C. J., *A revision of the Macronesian genus Argyranthemum Webb ex Schults Bip. (Compositae-Anthimideae)*, Bulletin of the British Museum (Natural History), Botany, 5:145-243 (1976) and Fjellheim, S., Holten Jorgensen, M., Kjos, M., Borgen, L. *A molecular study of hybridization and homoploid hybrid speciation in Argyranthemum (Asteraceae) on Tenerife, the Canary Islands*, Botanical Journal of the Linnean Society 159(1):19-31, 2009.

Over time plants are more accurately described and investigated by taxonomists who thereby impose changes to the generic and specific names. In the genus *Glebionis* there are currently two species, *G. coronaria* and *G. segetum*, according to Mabberley, D. J., Mabberley's Plant Book, Cambridge University Press, (2008). However, these species have also been historically included in *Chrysanthemum* and *Xanthopthalmum*. In the genus *Ismelia* there is currently only one species, *I. versicolor*. Historically this species has been known as *Chrysanthemum carinatum, Glebionis carinatum*, and *Ismelia versicolor*. To avoid confusion, in this application the convention of Mabberley 2008 applies where the genus *Glebionis* includes two species, *G. coronaria* and *G. segetum*, and the genus *Ismelia* includes one species, *I. versicolor*.

The complexity of inheritance influences the choice of breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Backcross breeding has been used to transfer traits that follow simple Mendelian inheritance into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed back (backcrossed) to the recurrent parent. The resulting plant is expected to have the attributes of the recurrent parent (e.g., cultivar) and the desirable trait transferred from the donor parent.

Pedigree breeding is used commonly for the improvement of self-pollinating crops. Two parents that possess favorable, complementary traits are crossed to produce an $F_1$ population. An $F_2$ population is produced by selfing one or several $F_1$ plants. Selection of the best individuals can begin in the $F_2$ population. Then, beginning in the $F_3$ generation, the best individuals in the best families are selected. Replica testing of families can begin in the $F_4$ generation to improve the effectiveness of selection for traits with low heritability. At an advanced stage of inbreeding (i.e., $F_6$ and $F_7$ generations), the best lines or mixtures of phenotypically similar lines are tested for potential release as new cultivars.

Pedigree breeding and recurrent selection breeding methods are used to develop cultivars from breeding populations. Breeding programs combine desirable traits from two or more cultivars or various broad-based sources into breeding pools from which cultivars are developed by selfing and selection of desired phenotypes. The new cultivars are evaluated to determine which have commercial potential.

Mass and recurrent selections can be used to improve populations of either self-pollinating or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Descriptions of other breeding methods that are commonly used for different traits and crops can be found in one of several reference books (e.g., Allard, R. W., *Principles of Plant Breeding*, John Wiley and Sons Inc. (1960); Simmonds, N. W., *Principles of Crop Improvement*, Longman Group, New York, USA (1981)).

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for three or more years. The best lines are candidates for new commercial cultivars. Those still deficient in a few traits can be used as parents to produce new populations for further selection.

These processes, which lead to the final step of marketing and distribution, require several steps from the time the first cross is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and/or to a common cultivar. If a single observation is inconclusive, repeated observations can provide a better estimate of its genetic worth.

Interspecific hybridization has allowed creation of new forms of plants and the transfer of desirable features from one species into another, for example, by introgression from wild species to related cultivated species. However, the ability of any two species to create viable interspecific hybrid seeds or plants is unpredictable and often has proved impossible.

Intergeneric hybridization, the crossing of two plants from different genera, is more unpredictable and improbable than interspecific hybridization because the relative genetic distance is greater between genera than between species. Only a few successful intergeneric hybrids have been reported and they are frequently only possible through human intervention and the use of embryo rescue. One form of embryo rescue is ovule culture, which involves aseptically removing the ovule from the seed and placing the ovule onto artificial media to enable the embryo to germinate and grow into a plant. In *Argyranthemum*, intergeneric hybrids have been reported between a female diploid *A. frutescens* and a male diploid *G. carinatum* (syn. *I. versicolor*) and between a female diploid *A. frutescens* and a male diploid *G. coronaria*, all developed by ovule culture (Ohtsuka, H. and Inaba, Z., *Intergeneric hybridization of marguerite (Argyranthemum futescens) with annual chrysanthemum (Glebionis carinatum) and crown daisy (G. coronaria) using ovule culture*, Plant Biotechnology, 25, 535-539 (2008); Ohtsuka, H. and Inaba, Z., *Breeding of Argyranthemum by interspecific and intergeneric hybridization*. 1. *Intergeneric hybridization of Argyranthemum and Ismeria carinata (syn. Chrysanthemum carinatum), I. coronaria (syn. Chrysanthemum coronaria) through ovule culture*, Journal of the Japanese Society for Horticultural Science, 72 (Suppl. 1), p. 264 (2003); Iwazaki, Y., Ueda, Y., and Yamada, H., *Studies on the acquisition method of an intergeneric hybridization of Argyranthemum and Ismelia by ovule culture*, Horticultural Research (Japan), 6 (Suppl. 1), p. 212 (2007)). However, the rate of efficiency (number of pollinations performed versus number of flowering plants produced) and quality of the plants produced is very low.

For example, Ohtsuka and Inaba (2008) reported that from 70 pollinations of *A. frutescens*×*G. carinatum* (syn. *I. versicolor*), only 16 embryos were obtained and germinated via ovule culture, and of those only five flowering plants developed. These five plants had similar morphology to *G. carinatum* (syn. *I. versicolor*). However, two died after flowering and the remaining three had pale green foliage, indicating weak growth. Ohtsuka and Inaba (2008) also reported that from 61 pollinations of *A. frutescens*×*G. coronaria*, only 26 embryos were obtained and germinated via ovule culture, and of those only 16 flowering plants developed. These 16 plants were generally characterized by upright vigorous growth with few branches, and pale green foliage with white or white/yellow ray floret color. Ohtsuka and Inaba (2008) further explain that from this cross combination "we were unable to find novel characteristics that might be valuable for flowerbed and pot plant production."

The present invention yielded the surprising discovery that commercially useful progeny could be developed from cross combinations using a female plant selected from the group *Ismelia versicolor* and *Glebionis* sp. crossed with a male *Argyranthemum* aneu-tetraploid plant. These crosses, in addition to being successful for *Ismelia versicolor, Glebionis coronaria* and *Glebionis segetum*, also surprisingly caused the female parents to self pollinate. Considering all of these species exhibit self-incompatibility (Anderson, N. O., Liedl, B. E., Ascher, P. D., Widmer R. E., and Desborough, S. L. (1988), *Evaluating self-incompatibility in Chrysanthemum*, Sexual Plant Reproduction 1: 173-181), it appears the stigmatic incompatability mechanism was overcome by the application of *Argyranthemum* pollen.

The present invention was unexpected because under conditions of intergeneric hybridization it is common to experience unilateral incongruity (Liedl, B and Anderson, N (1993). *Reproductive barriers: Identification, uses and circumvention*. In: Plant Breeding Reviews, 11: 11-154). That is to say, the cross will work in one direction, but not in the reciprocal. The reasons for this phenomenon can include various types of incompatibilities, and differences in endosperm balance number. In addition to useful intergeneric hybrid progeny, a large number of selfed progeny were produced by the act of pollinating the female *Glebionis* sp. and *I. versicolor* flowers with *Argyranthemum* pollen. This phenomenon has not been previously reported within the genera herein described.

The present invention provides another avenue for creating novel intergeneric hybrid plants and could assist in the development of such characteristics as increased capitula diameter, male sterility, female sterility, improved heat tolerance, perpetual flowering, new flower colours and brighter flower colours. Prior to the present invention, there have been no previous reports of successful hybridization at any ploidy level for plants from the group *Ismelia versicolor* and *Glebionis* sp. used as female parents crossed with *Argyranthemum* plants as male parents.

The foregoing examples of the related art and limitations related therewith are intended to be illustrative and not exclusive. Other limitations of the related art will become apparent to those of skill in the art upon a reading of the specification.

SUMMARY OF THE INVENTION

The following embodiments and aspects thereof are described in conjunction with systems, tools, and methods which are meant to be exemplary and not limiting in scope. In various embodiments, one or more of the above-described problems have been reduced or eliminated, while other embodiments are directed to other improvements.

One aspect of the present invention promotes the development of intergeneric hybrid plants by utilizing an *Argyranthemum* aneu-tetraploid plant as a male parent in crosses with *Glebionis* sp. and *I. versicolor* plants as female parents. The number of progeny resulting from the method of the present invention was unexpectedly high and the progeny were morphologically distinguished into two types, (1) those that were the result of self pollination and (2) those that were hybrids based on possessing morphological characteristics of both parents. It appeared that the *Argyranthemum* pollen facilitated the breakdown of the self-incompatability mechanism at the stigma of the *Glebionis* sp. and *I. versicolor* plants allowing self pollen to penetrate the stigma and effect fertilisation. In addition to the large number of self progeny, a small number of hybrid progeny were found. Further modifications could be utilized to reduce the number of self progeny and increase the number of hybrid progeny. Several methods are well known in the art and include, but are not limited to developing male sterile female parents, application of gametocides, emasculation to leave only the female ray florets, or pollen removal by washing with water or blowing with air. The techniques of the present invention provide a means to develop new types of intergeneric hybrids and a means to develop self progeny from *Glebionis* sp. and *I. versicolor*. Prior to the present invention, there have been no previous reports of successful hybridization at any ploidy level for a *Glebionis* sp. or *I. versicolor* female plant crossed with *Argyranthemum* as a male parent or for the development of self progeny from *Glebionis* sp. and *I. versicolor*. It is a further aspect of the present invention to provide an intergeneric hybrid plant produced from a cross between an aneu-tetraploid *Argyranthemum* plant as a female parent with a plant from the group consisting of *I. versicolor* and *Glebionis* sp. as a male parent.

It is a further aspect of the present invention to provide an intergeneric hybrid plant produced from a cross between plants from the group consisting of *I. versicolor* and *Glebionis* sp. as a female parent and an aneu-tetraploid *Argyranthemum* plant as a male parent.

It is a further aspect of the present invention to provide a plant part of an intergeneric hybrid plant produced from a cross between a plant from the group consisting of *I. versicolor* and *Glebionis* sp. as a female parent and an *Argyranthemum* plant as a male parent. It is a further aspect of the present invention to provide an intergeneric cross to produce a hybrid plant or part thereof which is clonally propagated.

It is a further aspect of the present invention to provide a method of producing an intergeneric hybrid plant comprising crossing a plant from the group consisting of *I. versicolor* and *Glebionis* sp. as a female parent and an *Argyranthemum* plant as a male parent, rescuing an embryo resulting from the crossing, and obtaining an intergeneric hybrid plant grown therefrom.

It is a further aspect of the present invention to provide a method for producing an intergeneric hybrid plant comprising the steps of: (a) cultivating first and second plants, wherein the first plant is an aneu-teraploid *Argyranthemum* plant and the second plant is from the group consisting of *I. versicolor* and *Glebionis* sp.; (b) collecting pollen from the first plant; (c) pollinating a capitulum on the second plant with this pollen; (d) isolating an embryo and germinating on suitable media in vitro; and (e) obtaining an intergeneric hybrid plant resulting from the growth of this embryo.

It is a further aspect of the present invention to provide a method for producing an intergeneric hybrid plant comprising the steps of: (a) obtaining a cutting of an intergeneric hybrid *Argyranthemum* plant, wherein said intergeneric hybrid is produced from the cross of a plant from the group consisting of *Ismelia versicolor, Glebionis coronaria*, and *Glebionis segetum* as a female parent and an aneu-tetraploid *Argyranthemum* male parent; and (b) cultivating this cutting to obtain an intergeneric hybrid *Argyranthemum* plant.

It is a further aspect of the present invention to provide a method for producing an intergeneric hybrid plant further defined by applying a plant hormone composition to the cutting base to induce the formation of roots to produce an intergeneric hybrid plant.

It is a further aspect of the present invention to provide a method for altering the chromosome number of an *Argyranthemum* plant to increase the somatic chromosome number from diploid 2n=2x=18 to aneu-tetraploid 2n=4x=32, 33, 34, 35, 37, to 38 comprising the steps of: (a) cultivating the *Argyranthemum* plant; (b) applying an anti-mitotic agent to the growing points of said plant; (c) forcing shoots to emerge from the treated growing points; (d) selecting putative aneu-tetraploid shoots thus developed; (e) assessing the chromosome complement of said shoots through cytological karyotype analysis; (f) growing said shoot into a plant; and (g) checking chromosomal stability.

It is a further aspect of the present invention to provide a method of altering the chromosome number of an *Argyranthemum* plant where the altered chromosome number is defined as being aneu-tetraploid to produce an aneu-tetraploid plant. A plant part of the aneu-tetraploid *Argyranthemum* plant is a flower, cutting, seed, pollen, ovule, or cell. A plant is then clonally propagated from the plant part.

It is a further aspect of the present invention to provide a plant of the genus *Argyranthemum*, preferably one with appropriate genetic characteristics useful for breeding for target traits (e.g., male and female fertility, suitable habit, earliness to flower, capitulum size and color, flowering period, capitulum form, etc.).

It is a further aspect of the present invention to develop an aneu-tetraploid form of an *Argyranthemum* plant, preferably by use of colchicine or other polyploidy inducing agent(s).

It is a further aspect of the present invention to stabilize and confirm an aneu-tetraploid plant, preferably by chromosome counts and/or by morphological changes to the plant, such as increased overall capitulum diameter, increased capitulum disk diameter, increased peduncle width, larger leaf size, and larger pollen diameter when compared to the diploid progenitor.

It is a further aspect of the present invention that the aneu-tetraploid plant of the present invention has a chromosome number ranging from 32, 33, 34, 35, 37, to 38.

It is a further aspect of the present invention that the intergeneric hybrid plant of the present invention has a chromosome number of 14, 15, 16, 17, 18, 19, 20, 21, 22, 23, 24, 25, 26, or 27.

It is a further aspect of the present invention to develop an aneu-triploid $F_1$ hybrid plant by crossing an aneu-tetraploid *Argyranthemum* plant with a plant from the group consisting of *I. versicolor* and *Glebionis* sp., collecting pollen from the $F_1$ hybrid and applying that pollen to an aneu-tetraploid *Argyranthemum* plant to obtain a back cross hybrid $F_2$ plant.

It is yet a further aspect of the present invention to cross *I. versicolor, Glebionis segetum* and *Glebionis coronaria* in all possible combinations to produce $F_1$ hybrid plants, select a hybrid plant and use the pollen from this hybrid plant to pollinate an aneu-tetraploid *Argyranthemum* plant to produce an aneu-triploid hybrid plant.

It is a further aspect of the present invention to infect aneu-triploid *Argyranthemum* hybrid plants with *Chrysanthemum* Virus B (CVB) and *Chrysanthemum* Stunt Viroid (CSVd).

In addition to the exemplary aspects and embodiments described above, further aspects and embodiments will become apparent by study of the following descriptions.

DETAILED DESCRIPTION OF THE INVENTION

In the description and tables that follow, a number of terms are used. In order to provide a clear and consistent understanding of the specification and claims, including the scope to be given such terms, the following definitions are provided:

Allele. An allele is any of one or more alternative forms of a gene which relate to one trait or characteristic. In a diploid cell or organism, the two alleles of a given gene occupy corresponding loci on a pair of homologous chromosomes.

Amiprophos-methyl (APM). As used herein, amiprophos-methyl (APM) refers to a compound used in plant breeding to induce chromosome doubling.

Androecium. Male parts of a plant flower which are collectively termed the stamens.

Anemone. A capitulum possessing disk florets which have elongated corolla tubes. Anemone type capitula appear intermediate in form between a normal (single) and a double flowered capitula. Anemone capitula are distinct from double flowered capitula wherein the latter, petals have replaced the stamens in the disk florets.

Aneu-tetraploid. As used herein, aneu-tetraploid means any plant having more or less than four times the monoploid chromosome number. For example, aneu-tetraploid *Argyranthemum* plants of the present invention have 32, 33, 34, 35, 37, or 38 chromosomes.

Aneu-triploid. As used herein, aneu-triploid means a triploid plant and any plant having more or less than three times the monoploid chromosome number. For example, aneu-triploid plants of the present invention have 23, 24, 25, 26, 27, 28, or 29 chromosomes.

Anti-miotic agent. As used herein, anti-miotic refers to a compound or chemical that is used to block cell growth by stopping mitosis (cell division) used in plant breeding to induce chromosome doubling. Examples of anti-miotic agents include, but are not limited to, colchicine, trifluralin, oryzalin, and amiprophos-methyl (APM).

Apomixis. Replacement of normal sexual reproduction by asexual reproduction without fertilization. In flowering plants, the term apomixis is commonly used to specify asexual reproduction through seeds.

*Argyranthemum*. As used herein, *Argyranthemum* refers to a genus of plants from the Asteraceae family. The *Argyranthemum* genus includes, but is not limited to, approximately 24 species (Humphries, C. J., *A revision of the Macronesian genus Argyranthemum Webb ex Schults Bip. (Compositae-Anthimideae)*, Bulletin of the British Museum (Natural History), Botany, 5:145-243 (1976)), including *A. adauctum, A. broussonetii, A. callichrysum, A. coronopifolium, A. dissectum, A. escarrei, A. fjlifolium, A. foeniculaceum, A. frutescens, A. gracile, A. haemotomma, A. haouarytheum, A. hierrense, A. lemsii, A. lidii, A. madarense, A. pinnatifidum, A. sventenii, A. sundingii, A. thalassophilum, A. tenerifae, A. vincentii, A. webbii*, and *A. winteri*.

Asexual propagation/Asexual reproduction. Asexual propagation or reproduction means every type of plant propagation except for sexually produced seeds. Examples of asexual propagation include, but are not limited to, cuttings, grafting, division, apomixis, or regeneration in tissue culture.

Backcrossing. Backcrossing is a process in which a breeder repeatedly crosses hybrid progeny back to one of the parents. For example, a first generation hybrid $F_1$ with one of the parental genotypes of the $F_1$ hybrid.

Bridging cross. A method of bypassing an incompatibility barrier between two genotypes or species by using a third genotype or species, which is partly compatible with each of them, in an intermediate cross.

Capitulum. Capitulum refers to an inflorescence in the form of a central disc of sessile flowers called disc florets and an outer ring of petal-like structures called ray florets. The disc florets are generally perfect while the ray florets are generally imperfect. The plural form of capitulum is capitula.

Cell. As used herein, cell includes a plant cell, whether isolated, in tissue culture, or incorporated in a plant or plant part.

Chimera. A chimera or a chimeric plant is a plant that consists of two or more genetically distinct groups of cells. The genetic distinctness usually originates from a mutation.

Chromosome number. The number of chromosomes possessed by a plant cell.

Chromosomal stability. As used herein, chromosomal stability refers to a chromosome that is not subject to sudden or extreme change or fluctuation.

*Chrysanthemum* Stunt Viroid (CSVd). The causal agent of the disease '*chrysanthemum* stunt', which causes stunting of growth in infected plants, including reduced flower size and premature flowering.

*Chrysanthemum* Virus B (CVB). A virus causing leaf-mottling or vein-clearing in infected plants.

Colchicine. Colchicine is a pale-yellow alkaloid, $C_{22}H_{25}NO_6$, obtained from the autumn *crocus* and used in plant breeding to induce chromosome doubling.

Cutting. A part originating from a plant, such as a stem, leaf, or root, removed from a plant to propagate a new plant, as through rooting or grafting.

Diploid. A diploid (denoted by the somatic cell chromosome number 2n=2x) is a somatic cell or plant having one pair of each type of chromosome (homologous pair), so that the basic (monoploid) chromosome number (denoted by the symbol x) is doubled.

Disc floret. One of the small tubular, actinomorphic florets which make up the central part of the capitulum in Compositae or Asteraceae plants.

Dominant inheritance. Refers to a mode of inheritance in which the phenotype of a certain characteristic or trait is determined by a dominant allele.

Dominant mutation. The phenotype of a dominant mutation is visible in a heterozygous genotype.

Double flower. A capitulum possessing disk florets where one or more petals have replaced the stamens.

Emasculation. The removal of the anthers of a flower to prevent self pollination.

Embryo. The young plant individual after fertilization or parthenogenesis when the proembryo has differentiated into embryo and suspensor.

Embryo culture. The growth of isolated plant embryos on suitable media in vitro.

Embryo rescue. As used herein, embryo rescue is the process plant breeders use to attempt to germinate embryos that may be weak, immature, or would otherwise not develop into a mature viable seed on the parent plant. For example, one form of embryo rescue is ovule culture, which involves aseptically removing the ovule from the seed and placing the ovule onto artificial media to enable the embryo to germinate and grow into a plant.

$F_2$. The "$F_2$" symbol denotes a generation resulting from the selfing of the $F_1$ generation. The "F" number is a term commonly used in genetics, and designates the filial generation. The "$F_2$" generation denotes the offspring resulting from the selfing or self mating of members of the first generation, the $F_1$ generation.

Gamete. A cell or nucleus that may participate in sexual fusion to form a zygote.

Gene. As used herein, gene refers to a segment of nucleic acid. A gene can be introduced into a genome of a species, whether from a different species or from the same species, using transformation or various breeding methods.

Gene-environment interaction/Genotype-environment interaction. Refers to the phenotypic effect of interactions between genes and the environment.

Genetic transformation. Refers to the genetic alteration of a cell resulting from the uptake, genomic incorporation, and expression of foreign genetic material.

Gene converted (Conversion). Gene converted (conversion) plants refers to plants which are developed by a plant breeding technique called backcrossing wherein essentially all of the desired morphological and physiological characteristics of a variety are recovered in addition to the one or more genes transferred into the variety via the backcrossing technique, genetic engineering, or mutation.

Genotype. Refers to the genetic constitution of a cell or organism.

*Glebionis* sp. As used herein, *Glebionis* sp. refers to a genus of plants from the Asteraceae family which includes, but is not limited to, *Glebionis coronaria*, also known as Crown Daisy, and *Glebionis segetum*, also known as the Corn Marigold (Mabberley 2008). Previous generic names included *Xanthopthalmum* and *Chrysanthemum*.

Gynoecium. The ovule producing parts of a plant's flower.

Haploid. A haploid is a cell nucleus containing only one representative of each chromosome of the chromosome complement, denoted by the symbol n. The haploid number (n) is the number of chromosomes in a haploid cell nucleus. Gametes are haploid cells.

Heterozygous. Refers to a genetic constitution in which the corresponding alleles of a certain gene locus are different.

Higher growing temperatures. As used herein, higher growing temperatures refers to the ability of progeny plants to grow and withstand temperatures greater than temperatures the parents used to produce the progeny were able to withstand.

Homozygous. Refers to a genetic constitution in which the corresponding alleles of a certain gene locus are identical.

Inbreeding. Is defined as the production of offspring by the fusion of genetically closely related gametes.

Inbreeding depression. Inbreeding depression is the reduced fitness in a given population as a result of breeding of close relatives or in plants also resulting from self pollination. It commonly occurs in species that are normally outbreeding.

Inflorescence. A group or cluster of flowers arranged on a stem that is composed of a main branch or an arrangement of branches.

Intergeneric cross. Intergeneric cross means the sexual hybridization of two individuals, each from a different genus. For example, an *Argyranthemum* plant crossed with an *Ismelia versicolor* plant.

Intergeneric hybrid. Intergeneric hybrid means a plant of the $F_1$ generation resulting from an intergeneric cross or a cross between two different genera.

Interspecific cross. Interspecific cross means the sexual hybridization of two individuals, each from different species of the same genus. For example, a *Glebionis coronaria* plant crossed with a *Glebionis segetum* plant.

Interspecific hybrid. Interspecific hybrid means a plant of the $F_1$ generation resulting from an interspecific cross or a cross between two different species.

*I. versicolor*. As used herein, *I. versicolor* refers to a genus of plants from the Asteraceae family which includes, but is not limited to, *Ismelia versicolor*, also known as Tricolor Daisy (Mabberley 2008). Previous genus and species names used for *Ismelia versicolor* include *Glebionis carinata*, *Glebionis carinatum*, and *Chrysanthemum carinatum*.

Karyotype analysis. As used here, karotype analysis means the ascertainment of chromosome number and constitution by light microscopy analysis of stained metaphase chromosomes. Cells are collected, induced to divide, and then arrested at metaphase (a stage of cell division when the chromosome are condensed and therefore visible). The chromosomes are stained with certain dyes that show a pattern of light and dark bands. Large changes in chromosomes can be detected using karyotype analysis.

Locus. A locus confers one or more traits such as, for example, herbicide tolerance, insect resistance, disease resistance, flower color, flower shape, plant height, etc. The trait may be, for example, conferred by a naturally occurring gene introduced into the genome of the variety by backcrossing, a natural or induced mutation, or a transgene introduced through genetic transformation techniques. A locus may comprise one or more alleles integrated at a single chromosomal location.

$M_0$. The $M_0$ generation is the generation treated with a mutagen. Subsequent generations are designated $M_1$, $M_2$, $M_3$, etc.

Monogenic inheritance. Refers to a mode of inheritance in which the phenotype of a certain characteristic or trait is determined by a single gene.

Monoploid. The monoploid chromosome number is the number of chromosomes in a single (non-homologous) set (x) and can be different from the haploid (n) number.

Mutation. Mutations are changes in the DNA sequence of a cell's genome and are caused by mutagens, like radiation or chemicals, as well as by errors that occur during DNA replication.

Oryzalin. As used herein, oryzalin refers to a compound used in plant breeding to induce chromosome doubling.

Outbreeding. Also known as outcrossing, is described as the production of offspring by the fusion of distantly related gametes. Outbreeding is the opposite of inbreeding.

Ovule culture. The culture of excised ovules on suitable media in vitro.

Phenotype. Refers to any observable characteristic or trait of a plant, such as flower color, plant size, etc.

Plant. As used herein, the term plant includes reference to an immature or mature whole plant, including a plant from which seed or anthers have been removed. Seed or embryo that will produce the plant is also considered to be the plant.

Plant hormone composition. As used herein, a plant hormone composition refers to a chemical that regulates plant growth. For example, Indole-3-butyric acid, $N^6$-benzyl adenine, and gibberellic acid.

Plant parts. As used herein, the term plant parts includes, but is not limited to, protoplasts, leaves, stems, roots, root tips, anthers, pistils, seed, embryo, pollen, ovules, cotyledon, hypocotyl, capitulum, ray petal/floret, disc petal/floret, shoot, tissue, petiole, cells, meristematic cells, and the like.

Pollination. Pollination is the process by which pollen is transferred in plants, thereby enabling fertilization and sexual reproduction.

Progeny. As used herein, progeny includes an $F_1$ plant produced from the cross of an *Argyranthemum* plant and a plant from the group consisting of *I. versicolor* and *Glebionis* sp. Progeny further includes, but is not limited to, subsequent $F_2$, $F_3$, $F_4$, $F_5$, $F_6$, $F_7$, $F_8$, $F_9$, and $F_{10}$ generational crosses with the parents and between the progeny.

Protoplast fusion/Somatic fusion. Refers to a breeding method in plants by which protoplasts (i.e., plant cells without cell walls) from two different plants are fused together to form a new hybrid plant with the characteristics of both.

Quantitative Trait Loci (QTL). Quantitative trait loci (QTL) refer to genetic loci that control to some degree numerically representable traits that are usually continuously distributed.

Ray floret. A ray floret or ligulate floret, is one of the outer, irregular florets in the capitulum of some Compositae or Asteraceae plants. In some Asteraceae or Compositae plants, the ligule of a ray floret is referred to as a petal.

Recessive inheritance. Refers to a mode of inheritance in which the phenotype of a certain characteristic or trait is determined by a recessive allele.

Recessive mutation. The phenotype of a recessive mutation is visible only in a homozygous genotype.

Regeneration. Regeneration refers to the development of a plant from tissue culture.

Sexual propagation/Sexual reproduction. Refers to the propagation of plants from seeds.

Somatic cell. Any cell of a plant other than the spores, gametes, or their precursors.

Tetraploid. As used herein, tetraploid refers to a cell or plant having a chromosome number that is four times the monoploid number of chromosomes. The chromosome number of the tetraploid *Argyranthemum* is 36, and is designated in somatic cells by 2n=4x.

Trifluralin. As used herein, trifluralin refers to a compound used in plant breeding to induce chromosome doubling.

Triploid. As used herein, a triploid refers to a cell or plant having a chromosome number that is three times the monoploid number of chromosomes. The chromosome number of the triploid is 27 and is designated in somatic cells by 2n=3x.

The following embodiments and aspects thereof are described in conjunction with systems, tools, and methods which are meant to be exemplary and not limiting in scope. In various embodiments, one or more of the above-described problems have been reduced or eliminated, while other embodiments are directed to other improvements.

In one aspect of the present invention new plants were produced with unique characteristics desirable for use as ornamental plants. These new plants of the present invention are intergeneric hybrids, not previously known, created in Yellow Rock, New South Wales, Australia. The plants were produced from the unexpected finding that intergeneric hybrid plants can be efficiently produced from the cross of plants from the group *I. versicolor* and *Glebionis* sp. as female parents and *Argyranthemum* plants as male parents.

The present invention provides another avenue for developing novel intergeneric hybrid plants with *Argyranthemum*. Previously there has not been a successful hybridization reported at any ploidy level for *I. versicolor* and *Glebionis* sp. crossed with any *Argyranthemum*.

It is a further aspect of the present invention to provide an intergeneric hybrid plant produced from a cross between a plant from the group consisting of *Ismelia versicolor*, also known as Tricolor Daisy, *Glebionis coronaria*, also known as Crown Daisy and *Glebionis segetum*, also known as the Corn Marigold as a female parent with an *Argyranthemum* plant as a male parent.

It is a further aspect of the present invention to provide an intergeneric hybrid plant produced from a cross between a plant from the group consisting of *Ismelia versicolor*, also known as Tricolor Daisy, *Glebionis coronaria*, also known as Crown Daisy and *Glebionis segetum*, also known as the Corn Marigold as a male parent with an *Argyranthemum* plant as a female parent.

It is a further aspect of the present invention to provide a plant part of an intergeneric cross hybrid aneu-triploid plant produced from a cross between a plant from the group consisting of *I. versicolor* and *Glebionis* sp. as a female parent and an *Argyranthemum* plant as a male parent.

It is an aspect of the present invention to provide an intergeneric cross to produce a hybrid plant or part thereof clonally propagated.

It is a further aspect of the present invention to provide a method of producing an intergeneric cross hybrid aneu-triploid plant comprising crossing a plant from the group consisting of *I. versicolor* and *Glebionis* sp. as a female parent with an *Argyranthemum* plant as a male parent, rescuing an embryo resulting from the crossing, and obtaining an intergeneric hybrid plant grown therefrom.

It is a further aspect of the present invention to provide a method of producing an intergeneric cross hybrid aneu-triploid plant comprising crossing a plant from the group consisting of *I. versicolor* and *Glebionis* sp. as a male parent with an *Argyranthemum* plant as a female parent, rescuing an embryo resulting from the crossing, and obtaining an intergeneric hybrid plant grown therefrom.

It is a further aspect of the present invention to provide a method for producing an intergeneric hybrid plant comprising the steps of: (a) cultivating first and second plants wherein the first plant is a plant from the group consisting of *I. versicolor* and *Glebionis* sp. and the second plant is an *Argyranthemum* plant; (b) collecting pollen from the second plant; (c) pollinating a capitulum on the first plant with this pollen; (d) isolating an embryo and germinating on suitable media in vitro; and (e) obtaining an intergeneric hybrid plant resulting from the growth of this embryo.

It is a further aspect of the present invention to provide a method for producing an intergeneric hybrid plant comprising the steps of: (a) obtaining a cutting of an intergeneric hybrid plant, produced from the cross a plant from the group consisting of *Ismelia versicolor, Glebionis coronaria* and *Glebionis segetum* as a female parent and an *Argyranthemum* male parent; and (b) cultivating this cutting to obtain an intergeneric hybrid plant.

It is a further aspect of the present invention to provide a method for producing an intergeneric hybrid plant further defined by applying a plant hormone composition to the cutting base to induce the formation of roots to produce an intergeneric hybrid plant.

It is a further aspect of the present invention to provide a method for altering the chromosome number of an *Argyranthemum* plant to increase the somatic chromosome number from diploid 2n=2x=18 to aneu-tetraploid 2n=4x=32, 33, 34, 35, 37, to 38 comprising the steps of: (a) cultivating the *Argyranthemum* plant; (b) applying an anti-mitotic agent to the growing points of said plant; (c) forcing shoots to emerge from the treated growing points; (d) selecting putative aneu-tetraploid shoots thus developed; (e) assessing the chromosome complement of said shoots through cytological karyotype analysis; (f) growing said shoot into a plant; and (g) checking chromosomal stability.

It is a further aspect of the present invention to provide a method of altering the chromosome number of an *Argyranthemum* plant where the altered chromosome number is defined as being aneu-tetraploid to produce an aneu-tetraploid plant. A plant part of the aneu-tetraploid *Argyranthe-*

*mum* plant is a flower, cutting, seed, pollen, ovule, or cell. A plant is then clonally propagated from the plant part.

It is a further aspect of the present invention to provide a plant of the genus *Argyranthemum*, preferably one with appropriate genetic characteristics useful for breeding for target traits (e.g., male and female fertility, suitable habit, earliness to flower, capitulum size and color, flowering period, flower form, etc.).

It is a further aspect of the present invention to develop an aneu-tetraploid form of an *Argyranthemum* plant, preferably by use of colchicine or other polyploidy inducing agent(s).

It is a further aspect of the present invention to stabilize and confirm an aneu-tetraploid plant, preferably by chromosome counts and/or by morphological changes to the plant, such as increased overall capitulum diameter, increased capitulum disk diameter, increased peduncle width, larger leaf size, and larger pollen diameter, when compared to the diploid progenitor.

It is a further aspect of the present invention that the aneu-tetraploid plant of the present invention has a chromosome number ranging from 32, 33, 34, 35, 37, to 38.

It is a further aspect of the present invention that the intergenetic hybrid plant of the present invention has a chromosome number of 14, 15, 16, 17, 18, 19, 20, 21, 22, 23, 24, 25, 26, or 27.

It is a further aspect of the present invention to develop an aneu-triploid $F_1$ hybrid by crossing an aneu-tetraploid *Argyranthemum* with a plant from the group consisting of *I. versicolor* and *Glebionis* sp., collecting pollen from the $F_1$ hybrid and applying that pollen to an aneu-tetraploid *Argyranthemum* plant to obtain a back-cross hybrid $F_2$ plant.

It is yet a further aspect of the present invention to cross *Ismelia versicolor, Glebionis segetum* and *Glebionis coronaria* in all possible combinations to produce $F_1$ hybrid plants, select a hybrid plant and use the pollen from this hybrid plant to pollinate an aneu-tetraploid *Argyranthemum* plant to produce an aneu-triploid hybrid plant.

Another further aspect of the current invention involves introducing a virus (*Chrysanthemum* Virus B, CVB) and a viroid (*Chrysanthemum* Stunt Viroid, CSVd) into an aneu-triploid *Argyranthemum* hybrid plant to alter the phenotype of said plant, thereby possibly improving its potential as a commercially viable product.

Further Embodiments of the Invention

In addition to the exemplary aspects and embodiments described above, further aspects and embodiments will become apparent by study of the following descriptions.

I. Development of Aneu-Tetraploid *Argyranthemum* sp.

The present invention provides a method for generating aneu-tetraploid *Argyranthemum* plants defined herein as having a chromosome number ranging from 32, 33, 34, 35, 37, to 38.

*Argyranthemum* plants are from any one of the following species or hybrids of the following species: *A. adauctum, A. broussonetii, A. callichrysum, A. coronopifolium, A. dissectum, A. escarrei, A. filifolium, A. foeniculaceum, A. frutescens, A. gracile, A. haemotomma, A. haouarytheum, A. hierrense, A. lemsii, A. lidii, A. madarense, A. pinnatifidum, A. sventenii, A. sundingii, A. thalassophilum, A. tenerifae, A. vincentii, A. webbii,* and *A. winteri.* An aneu-tetraploid form of an *Argyranthemum* plant is developed, preferably by use of an anti-miotic agent. Examples of anti-miotic agents include, but are not limited to, colchicine, trifluralin, oryzalin, amiprophos-methyl, and other polyploidy inducing agent(s). Tetraploids can occur spontaneously in nature or be induced using spindle fiber inhibitors, such as colchicine. The technique of colchicine-induced polyploidization has been used since the 1930's. Colchicine inhibits the assembly of tublin subunits into spindle fibers, such that no chromosome movement can occur and hence, cells at the metaphase stage of mitosis accumulate. When the chromatids separate, but are not divided into separate cells by the spindle, the chromosome number is doubled creating an autopolyploid. When creating a polyploid for breeding purposes, the layer of the apical meristem that gives rise to the gametophytic tissue needs to be doubled. To optimize the probability of successful doubling, a high number of small, actively growing meristems are treated. Usually colchicine is used at a concentration of 0.1% to 2.0% depending on the tissue and the species. Methods for treating seeds and plant parts with colchicine or other spindle fiber inhibitors are well-known in the art, as discussed in Poehlman, J. M., *Breeding Field Crops*, University of Missouri, Holt, Rinehart and Winston Inc. (1966); Watts, L., *Flower and Vegetable Plant Breeding*, Grower Books (1980); Callaway D. J. and Callaway M. B., *Breeding Ornamental Plants*, Timber Press Inc. (2000).

Ploidy changes affect crossability, fertility, cell size, and heterozygosity. These factors offer potential benefits as well as limitations in plant breeding. Ploidy manipulation was used for the introgression of germplasm between taxa of different ploidy. For example, to overcome $F_1$ sterility of interspecific *Lilium* hybrids, colchicine was used for the induction of tetraploids. Interspecific crosses at the tetraploid level between complex hybrids of four *Lilium* species were made. See, Van Tuyl, J. and van Holsteijn, H. *Lily breeding research in the Netherlands* Acta Horticulturae, 414: 35-45 (1996). Tetraploid plants of *Buddleja globosa*, which is naturally diploid, were produced using colchicine treatment and have been crossed with natural tetraploid *Buddleja davidii* to introduce yellow flower color into *Buddleja davidii*. See, Rose, J., Kubba, J. and Tobutt, K. *Induction of tetraploids for breeding hardy ornamentals*, Acta Horticulturae, 560: 109-112 (2001). All yellow-flowered *Cyclamen persicum* cultivars are diploid and do not have "eyes" on the petals. Using colchicine treatment, a tetraploid yellow-flowered cyclamen was induced. After crossing with tetraploid "eyed" cultivars, segregation was such that yellow-flowered "eyed" selections could not be maintained by seed. See, Takamura, T., Sugimura, T., Tanaka, M. and Kage, T. *Breeding of the yellow-flowered tetraploid cyclamen with "eye"*, Acta Horticulturae, 454: 119-126 (1998).

The present invention provides a method of altering the chromosome number of an *Argyranthemum* plant to develop an aneu-tetraploid plant, with a chromosome number ranging from 32, 33, 34, 35, 37, to 38 comprising the steps of: (a) cultivating the *Argyranthemum* plant; (b) applying an anti-mitotic agent to the growing points of the plant; (c) forcing shoots to emerge from the treated growing points of the plant; (d) selecting putative aneu-tetraploid shoots thus developed from the plant; (e) assessing the chromosome complement of the aneu-tetraploid shoots through cytological karyotype analysis; (f) growing the aneu-tetraploid shoot into a plant; and (g) checking chromosomal stability. It can be appreciated by one skilled in the art that the induction of tetraploidy can result in plants with chromosome numbers higher or lower than the expected tetraploid number and such aneuploid plants are herein defined as aneu-tetraploid and include plants with chromosome counts ranging from 32, 33, 34, 35, 37, to 38.

II. Production of Intergeneric Hybrid Plants

The flower industry strives to develop new and different varieties of flowering plants. An effective way to create such novel varieties is through the manipulation of flower color. Flower color is predominantly due to two types of pigment: flavonoids and carotenoids. Flavonoids contribute to a range of colors from yellow to red to blue. Carotenoids impart a reddish-orange or yellow tinge and are commonly the only pigment in yellow or orange flowers. The flavonoid molecules which make the major contribution to flower color are the anthocyanins, which are glycosylated derivatives of cyanidin, delphinidin, petunidin, peonidin, malvidin, and pelargonidin, and are localized in the vacuole. The different anthocyanins can produce marked differences in color. Flower color is also influenced by co-pigmentation with colorless flavonoids, metal complexation, glycosylation, acylation, methylation, and vacuolar pH. See, Forkman, G. *Flavonoids as flower pigments: the formation of the natural spectrum and its extension by genetic engineering*, Plant Breeding 106:1-26 (1991).

The present invention unexpectedly gave rise to intergeneric hybrid plants with novel flower colors and other useful attributes such as improved heat tolerance, larger capitula size, etc. The method of the present invention used plants from *Ismelia versicolor, Glebionis coronaria*, or *Glebionis segetum* as female parents in intergeneric crosses with *Argyranthemum* plants as the male parent, and wherein said cross comprised the following steps: (a) collecting pollen from the *Argyranthemum* plant; (b) pollinating a capitulum on the *I. versicolor* or *Glebionis* sp. female plant with this pollen; (c) isolating an embryo resulting from the pollination by embryo rescue; (d) in vitro culture of the embryo on nutrient agar medium; (e) obtaining an intergeneric hybrid plantlet resulting from the growth of this embryo; and (f) transplanting plantlets to a greenhouse growing medium where they developed into mature intergeneric hybrid plants. By using an aneu-tetraploid male *Argyranthemum* parent hybrid progeny were produced; however, the large majority of progeny were the result of self pollination with a lower number of true hybrids.

It is a further aspect of the present invention to provide a method comprising the steps of: (a) intercrossing plants in the group consisting of *Ismelia versicolor, Glebionis coronaria*, or *Glebionis segetum*, in all combinations and producing an embryo from said crosses; (b) using embryo rescue on said embryo; and (c) obtaining an interspecific hybrid plant that can then be used as a female parent in crossing with *Argyranthemum* male parents.

It is a further aspect of the present invention that the intergeneric hybrid plant of the present invention is aneu-diploid to aneu-triploid as defined herein with a chromosome number of 14, 15, 16, 17, 18, 19, 20, 21, 22, 23, 24, 25, 26, or 27.

It is a further aspect of the present invention to propagate an intergeneric hybrid plant comprising the steps of: (a) obtaining a cutting of an intergeneric hybrid plant produced from the cross of a plant from the group consisting of *Ismelia versicolor, Glebionis coronaria*, and *Glebionis segetum* as a female parent with an *Argyranthemum* plant as a male parent; and (b) cultivating this cutting to obtain an intergeneric hybrid plant.

It is a further aspect of the present invention to provide a method for producing an intergeneric hybrid plant further defined by applying a plant hormone composition to the cutting base to induce the formation of roots to produce an intergeneric hybrid plant.

III. Production of Intergeneric Hybrid Plants Using *Glebionis* sp.×*I. versicolor* Hybrids as Male Parents in a Bridging Cross It is often found in plant breeding that some plants will cross and others will not. For example, plant A will cross with plant B extremely well, but only rarely with plant C. However, plant B and C will cross readily. To introduce genes from plant C into a hybrid with plant A, a bridging cross can be performed. Under such circumstances plants B and C are intercrossed, $F_1$ hybrid plants are developed, pollen is collected from an $F_1$ hybrid plant and applied to the stigmas of plant A and a new hybrid plant is developed. The cross then is A×(B×C). This methodology was utilized to develop aneu-triploid intergeneric hybrids of the following combination: aneu-tetraploid *Argyranthemum*×(*Glebionis* sp.×*I. versicolor* in all possible combinations).

The present invention surprisingly allowed the development of aneu-triploid intergeneric hybrid plants with characteristics from at least three separate species, where one species is *Argyranthemum*, and the other two species are chosen from the group *G. segetum, G. coronaria* and *I. versicolor*.

IV. Backcrossing of Aneu-Triploid Intergeneric Hybrids

Ornamental plant breeding involves the development of new types of plants with novel characteristics. Under some circumstances, new plants developed cannot be used for further breeding work, due to such obstacles as incongruity, various incompatabilities, uneven chromosome number and other unknown factors. An example of this problem was found with the aneu-triploid intergeneric hybrids developed by crossing aneu-tetraploid *Argyranthemum*×*Ismelia versicolor*. Nearly all plants developed were male sterile (possessing no pollen). Surprisingly, a few plants were produced that possessed some pollen. Hybridisations were performed following the standard procedures previously described using pollen collected from the aneu-triploid $F_1$ hybrid plant and applying that pollen onto an aneu-tetraploid *Argyranthemum* capitulum to develop backcross progeny.

V. Infection of hybrid plants with *Chrysanthemum* Virus B (CVB) and *Chrysanthemum* Stunt Viroid (CSVd).

It is a further aspect of the present invention to infect aneu-triploid *Argyranthemum* hybrid plants with *Chrysanthemum* Virus B (CVB) and *Chrysanthemum* Stunt Viroid (CSVd). This may be achieved through grafting an infected plant to an unifected plant, allowing the graft to heal, then growing the newly infected plant and testing it via PCR and/or ELISA based methods to confirm infection status.

In addition to the exemplary aspects and embodiments described above, further aspects and embodiments will become apparent by study of the following examples.

EXAMPLES

The following examples are provided to further illustrate the present invention. These examples are not to be construed as limiting the scope of the invention in any manner beyond the limitations set forth in the appended claims. Many variations and modifications may be made while remaining within the spirit and the scope of the invention.

Example 1

Development of Aneu-Tetraploid *Argyranthemum* sp

The present invention provides a new method for altering the chromosome number of an *Argyranthemum* plant to double the somatic chromosome number from diploid to aneu-tetraploid. The method for altering the chromosome number of the present invention began with first cultivating an *Argyranthemum* plant and then an anti-mitotic agent, such as colchicine, trifluralin, oryzalin, or amiprophosmethyl (APM), was applied to the growing points of the *Argyranthemum* plant. Aneu-tetraploid shoots were then forced to emerge from the treated growing points of the *Argyranthemum* plant and the putative aneu-tetraploid shoots that had been developed from the growing points of the *Argyranthemum* plant were selected. The chromosome complement of the aneu-tetraploid shoots was then assessed through cytological karyotype analysis and the analyzed aneu-tetraploid shoots were then grown into a plant. Chromosomal stability of the new *Argyranthemum* plant was checked and the new aneu-tetraploid *Argyranthemum* plant was selected and maintained. Pollen was collected from the capitulum of an aneu-tetraploid *Argyranthemum* plant and then applied to the capitulum of a receptive *Glebionis* sp. or *I. versicolor* plant. An embryo was then rescued from the crossing and the rescued embryo was then isolated by embryo rescue in tissue culture and an intergeneric hybrid plant was produced from the tissue from the rescued embryo.

One aspect of the present invention involved the steps of obtaining a plant of the genus *Argyranthemum* with appropriate genetic characteristics useful for breeding for target traits, including, but not limited to, male and female fertility, suitable habit, earliness to flower, capitulum size and color, flowering period, and capitulum form. After the *Argyranthemum* plant was obtained, an aneu-tetraploid *Argyranthemum* plant was developed using the following method: 100 cuttings were collected from vegetatively growing stockplants, the cut bases were dipped in 2000 ppm Indole-butyric acid powder and then planted into Oasis® brand propagation wedges. The cuttings were then placed under intermittent mist in a propagation house maintained at approximately 20° C. After three weeks, the cuttings were acclimatized to greenhouse conditions and then one plant was potted into each of one hundred 10 cm diameter pots filled with a standard nursery potting mix. The potted plants were placed in a greenhouse at 15° C. minimum temperature. After about two weeks the plants were ready for colchicine application. Colchicine was prepared as a paste from 0.1%-2.0% weight/volume with a water soluble gel. A range of colchicine concentrations was used for treating the plants so that it could be determined which concentration gave optimal results for each line treated.

The paste was liberally applied to the buds and washed off using a fine water mist after 24 hours. The number of plants and buds painted was counted during application so that a measure of efficiency of production could be made upon completion.

For the next few weeks, plants were observed and maintained according to best practice and growth procedures (e.g., Hamrick, D. (Ed), *Ball Red Book, Crop Production Volume 2*, Ball Publishing (2003)). New shoots were assessed for signs of aneu-tetraploidy. These signs included: shoots with larger than normal foliage and wider petiole diameter, florets with larger stigmas, capitula with larger center disks, capitula with longer peduncle length and width, and florets with larger pollen diameter. Shoots that looked diploid were trimmed from the plants. Selected putative aneu-tetraploid shoots were labeled and trimmed to encourage further growth.

Once fresh putative aneu-tetraploid shoots were produced, cuttings were taken and propagated. These second generation plants were continually assessed for stability and uniformity of aneu-tetraploidy based on phenotype. Putative aneu-tetraploids were then confirmed or discarded by performing karyotype analysis. After confirmation, plants were propagated at least two more times to ensure they were stable aneu-tetraploids. On a regular basis, the plants were visually examined for morphological characteristics of tetraploidy. The morphological changes to the plants included, but are not limited to, increased overall capitula diameter, increased capitula disk diameter, increased peduncle width, larger leaf size, larger stigma size, and larger pollen diameter compared to the diploid progenitor. Chromosome counts were performed on selected lines of *Argyranthemum*, *Ismelia* sp. and *Glebionis* sp., and the intergeneric hybrids.

Example 2

Chromosome counts of *Argyranthemum*, *Ismelia*, and *Glebionis* lines

Table 1 below shows the chromosome counts of some *Argyranthemum*, *Ismelia*, and *Glebionis* lines. Column one shows the plant identification number, column two shows the genus and pedigree, column three shows the chromosome count range, and column four shows the confirmed ploidy level.

TABLE 1

Chromosome counts of some *Argyranthemum*, *Ismelia*, *Glebionis*, and colchicine treated *Argyranthemum* lines performed at meiosis (n), or mitosis (2n)

| Plant No. | Genus, pedigree | Chromosome count | Confirmed ploidy |
|---|---|---|---|
| 04-36 | *Argyranthemum* | n = 9 | diploid |
| 04-79 | *Argyranthemum* | n = 9 | diploid |
| 04-92 | *Argyranthemum* | n = 9 | diploid |
| 05-135 | *Argyranthemum* | n = 9 | diploid |
| 06-117 | *Argyranthemum* | n = 9 | diploid |
| 09-27 | *Glebionis segetum* | 2n = 18 | diploid |
| 10-19 | *Glebionis coronaria* | 2n = 18 | diploid |
| 10-20 | *Glebionis coronaria* | 2n = 18 | diploid |
| 08-80 | *Ismelia versicolor* | 2n = 18 | diploid |
| 08-81 | *Ismelia versicolor* | n = 9 | diploid |
| 08-82 | *Ismelia versicolor* | 2n = 18 | diploid |
| 08-119 | *Argyranthemum* 04-92, treated with colchicine | 2n = 36 | aneu-tetraploid |
| 08-124 | *Argyranthemum* 04-92, treated with colchicine | 2n = 36 | aneu-tetraploid |
| 09-20 | *Argyranthemum* 04-92, treated with colchicine | 2n = 32, 33, 34, 35, 36 | aneu-tetraploid |
| 09-21 | *Argyranthemum* 04-92, treated with colchicine | 2n = 36 | aneu-tetraploid |
| 09-2 | *Argyranthemum* 04-79, treated with colchicine | 2n = 36 | aneu-tetraploid |

TABLE 1-continued

Chromosome counts of some *Argyranthemum*, *Ismelia*, *Glebionis*, and colchicine treated *Argyranthemum* lines performed at meiosis (n), or mitosis (2n)

| Plant No. | Genus, pedigree | Chromosome count | Confirmed ploidy |
|---|---|---|---|
| 09-3 | *Argyranthemum* 04-79, treated with colchicine | 2n = 36, n = 18 | aneu-tetraploid |
| 09-4 | *Argyranthemum* 04-79, treated with colchicine | 2n = 36, n = 18 | aneu-tetraploid |
| 09-5 | *Argyranthemum* 04-79, treated with colchicine | 2n = 36 | aneu-tetraploid |
| 09-6 | *Argyranthemum* 04-79, treated with colchicine | 2n = 36 | aneu-tetraploid |
| 09-8 | *Argyranthemum* 05-135, treated with colchicine | n = 18 | aneu-tetraploid |
| 09-9 | *Argyranthemum* 05-135, treated with colchicine | n = 18 | aneu-tetraploid |
| 09-10 | *Argyranthemum* 05-135, treated with colchicine | 2n = 36, 37, 38 | aneu-tetraploid |
| 09-12 | *Argyranthemum* 05-135, treated with colchicine | 2n = 34, 35, 36 | aneu-tetraploid |
| 11-455 | *Argyranthemum* 04-36, treated with colchicine | 2n = 36 | aneu-tetraploid |
| 11-458 | *Argyranthemum* 04-36, treated with colchicine | 2n = 36 | aneu-tetraploid |
| 10-110 | *Argyranthemum* 06-117, treated with colchicine | 2n = 36 | aneu-tetraploid |

Example 3

Origin and Description of *Argyranthemum* Aneu-Tetraploid Lines Developed

Table 2 below provides the origin and a description of *Argyranthemum* aneu-tetraploid plants that were produced and then used in the breeding crosses shown in Tables 4-10. Diploid parent lines (shown in column one, phenotype shown in column two) were treated with variable amounts of colchicine, a chemical mutagen which can cause chromosome doubling. The aneu-tetraploid plants (shown by their identification number) that were selected for further breeding and analysis are shown in column three. The phenotype of the aneu-tetraploid lines are shown in column four.

Example 4

*Glebionis* sp. and *I. versicolor* Varieties and Hybrids Used in the Breeding Crosses Shown in Tables 4-10

Table 3 below provides the botanical name and a description of the *Glebionis* sp. and *I. versicolor* varieties and hybrids that were used in the breeding crosses shown in Tables 4-10. The botanical name is shown in column one, the plant identification number is shown in column two, and capitulum form and color is shown in column three.

TABLE 2

Origin and description of *Argyranthemum* aneu-tetraploid plants shown in Tables 1 and 4-10

| Diploid parent line | Phenotype of Diploid parent | Aneu-tetraploid ID No. | Phenotype of aneu-tetraploid parents compared to diploid progenitor |
|---|---|---|---|
| 04-36 | Anemone pink capitulum, compact habit, high branching, early flowering, high general combining ability | 11-455<br>11-458 | Single pink capitulum, compact habit, less branching, later flowering. Capitulum peduncle thicker and longer, larger foliage size. |
| 04-79 | Single white capitulum, compact habit and high branching, early flowering. | 09-3<br>09-4<br>09-5<br>09-6 | Single white capitulum, compact but less branching, later flowering. Capitulum peduncle thicker and longer, larger foliage size. |
| 04-92 | Anemone yellow capitulum, compact habit, high branching, mid flowering. | 08-124<br>08-129<br>09-20<br>09-21 | Anemone yellow capitulum, compact habit, high branching, later flowering. Capitulum peduncle thicker and longer, larger foliage size. |
| 05-76 | Single pale yellow capitulum, compact habit, medium branching, early flowering, low fertility | 10-114<br>10-115<br>10-117<br>10-121 | Single pale yellow capitulum, very compact habit, medium branching, later flowering. Capitulum peduncle thicker and longer, larger foliage size. |
| 05-135 | Single red capitulum, medium habit and medium branching, early flowering. | 09-8<br>09-10<br>09-12 | Single red capitulum, medium to upright habit, medium to low branching, later flowering. Capitulum peduncle thicker and longer, larger foliage size. |
| 06-117 | Single ivory capitulum, compact habit, high branching, early flowering, male sterile, high general combining ability | 10-105<br>10-106<br>10-108<br>10-110<br>10-112 | Single ivory capitulum, compact habit, less branching, later flowering, male sterile. Capitulum peduncle thicker and longer, larger foliage size. |

TABLE 3

Botanical name and description of *Glebionis* sp. and *I. versicolor* varieties and hybrids used in the breeding crosses shown in Tables 4-10

| Botanical name | ID No. | Capitulum form and color |
|---|---|---|
| *Ismelia versicolor* | CC2 | single, pink |
| *Ismelia versicolor* | CC3 | single, pink ring |
| *Ismelia versicolor* | CC4 | single, yellow |
| *Ismelia versicolor* | CC5 | single, yellow/red |
| *Glebionis coronaria* | CCo1 | single, lemon outer, yellow center |
| *Glebionis coronaria* | CCo2 | single, lemon outer, yellow center |
| *Glebionis coronaria* | CCo3 | single, yellow |
| *Glebionis segetum* | CS1 | single, yellow |
| *Glebionis segetum* | CS2 | single, yellow |
| *Ismelia versicolor* | 08-80 | single, orange/red ring |
| *Ismelia versicolor* | 08-81 | single, orange/yellow ring |
| *Ismelia versicolor* | 08-82 | single, deep red fades to orange |
| *Ismelia versicolor* | 08-83 | single |
| *Ismelia versicolor* | 08-86 | single, yellow with red edges |
| *Glebionis segetum* | 08-89 | single, yellow |
| *Glebionis segetum* | 09-27 | single, bright yellow |
| *Glebionis segetum* | 09-28 | single, cream with yellow ring |
| *Ismelia versicolor* | 10-12 | single, yellow with red edge to petals |
| *Ismelia versicolor* | 10-17 | single, orange/red over yellow |
| *Glebionis coronaria* | 10-18 | single, cream with yellow ring |
| *Glebionis coronaria* | 10-19 | single, bright yellow |
| *Glebionis coronaria* | 10-20 | single, cream with yellow ring |
| *Glebionis coronaria* | 10-21 | single, bright yellow |
| *I. versicolor* 10-12 × *G. segetum* 08-89 | 11-172 | single, yellow |
| *I. versicolor* 10-12 × *G. segetum* 08-89 | 11-203 | single, yellow |
| *I. versicolor* 08-81 × *G. coronaria* 10-20 | 11-176 | single, yellow |
| *I. versicolor* 08-81 × *G. coronaria* 10-20 | 11-179 | single, yellow |
| *G. segetum* 08-89 × *I. versicolor* 10-12 | 11-166 | single, yellow |
| *G. segetum* 09-27 × *I. versicolor* 08-81 | 11-167 | single, yellow |
| *G. coronaria* 08-83 × *I. versicolor* 08-81 | 11-184 | single, yellow with dark center |
| *G. coronaria* 08-83 × *I. versicolor* 10-17 | 11-186 | single, yellow with dark center |

Example 5

Comparing Efficiency of Production of Intergeneric Hybrid Plants Using Diploid *Argyranthemum* Female Parents and Aneu-Tetraploid *Argyranthemum* Female Parents Derived from the Same Genotypes×*Glebionis* sp. and *I. versicolor*

Comparative crosses were undertaken to determine the efficiency of production between using diploid and aneu-tetraploid female *Argyranthemum* parents. Four diploid *Argyranthemum* female parents were used. Aneu-tetraploid versions of these same accessions were developed and used as well. Crosses were performed using the diploid and aneu-tetraploid *Argyranthemum* plants as female parents and plants of *Glebionis* sp. and *I. versicolor* as male parents. The results were compared. Table 4A shows the number of capitula pollinated for each cross combination, Table 4B shows the number of embryos rescued and Table 4C shows the number of plants developed.

TABLE 4A

Number of capitula pollinated using diploid *Argyranthemum* female parents and aneu-tetraploid *Argyranthemum* female parents derived from the same genotypes × *Glebionis* sp. and *I. versicolor*.

| Line No. | Pedigree | *G. coronaria* 10-18 | *G. segetum* 09-27 | *I. versicolor* 08-80 | Total |
|---|---|---|---|---|---|
| 04-36 | Diploid | 3 | 3 | 3 | 36 |
| 04-79 | Diploid | 3 | 3 | 3 | |
| 04-92 | Diploid | 3 | 3 | 3 | |
| 06-117 | Diploid | 3 | 3 | 3 | |
| 11-455 | Aneu-tetraploid 04-36 | 3 | 3 | 3 | 36 |
| 09-5 | Aneu-tetraploid 04-79 | 3 | 3 | 3 | |
| 09-20 | Aneu-tetraploid 04-92 | 3 | 3 | 3 | |
| 10-110 | Aneu-tetraploid 06-117 | 3 | 3 | 3 | |

TABLE 4B

Number of embryos rescued using diploid *Argyranthemum* female parents and aneu-tetraploid *Argyranthemum* female parents derived from the same genotypes × *Glebionis* sp. and *I. versicolor*.

| Line No. | Pedigree | *G. coronaria* 10-18 | *G. segetum* 09-27 | *I. versicolor* 08-80 | Total |
|---|---|---|---|---|---|
| 04-36 | Diploid | 2 | 1 | 1 | 9 |
| 04-79 | Diploid | 0 | 0 | 0 | |
| 04-92 | Diploid | 0 | 0 | 0 | |
| 06-117 | Diploid | 0 | 0 | 5 | |

TABLE 4B-continued

Number of embryos rescued using diploid *Argyranthemum* female parents and aneu-tetraploid *Argyranthemum* female parents derived from the same genotypes × *Glebionis* sp. and *I. versicolor*.

| Line No. | Pedigree | G. coronaria 10-18 | G. segetum 09-27 | I. versicolor 08-80 | Total |
|---|---|---|---|---|---|
| 11-455 | Aneu-tetraploid 04-36 | 2 | 2 | 1 | 123 |
| 09-5 | Aneu-tetraploid 04-79 | 2 | 0 | 5 | |
| 09-20 | Aneu-tetraploid 04-92 | 10 | 1 | 17 | |
| 10-110 | Aneu-tetraploid 06-117 | 35 | 29 | 19 | |

TABLE 4C

Number of plants developed using diploid *Argyranthemum* female parents and aneu-tetraploid *Argyranthemum* female parents derived from the same genotypes × *Glebionis* sp. and *I. versicolor*.

| Line No. | Pedigree | G. coronaria 10-18 | G. segetum 09-27 | I. versicolor 08-80 | Total |
|---|---|---|---|---|---|
| 04-36 | Diploid | 0 | 1 | 0 | 2 |
| 04-79 | Diploid | 0 | 0 | 0 | |
| 04-92 | Diploid | 0 | 0 | 0 | |
| 06-117 | Diploid | 0 | 0 | 1 | |
| 11-455 | Aneu-tetraploid 04-36 | 0 | 1 | 1 | 77 |
| 09-5 | Aneu-tetraploid 04-79 | 0 | 0 | 3 | |
| 09-20 | Aneu-tetraploid 04-92 | 4 | 0 | 15 | |
| 10-110 | Aneu-tetraploid 06-117 | 30 | 14 | 9 | |

Tables 4A, B and C demonstrate the improved efficiency of production that can be obtained when using aneu-tetraploid *Argyranthemum* plants as female parents in cross combinations using *I. versicolor* and *Glebionis* sp. as male parents.

Example 6

Method for Species by Species Crossing—*Glebionis* sp. and *I. versicolor* Hybridization In a further aspect of the invention, the species *Glebionis coronaria*, *Glebionis segetum* and *Ismelia versicolor* were intercrossed in all possible pairwise combinations following the same procedures as described previously for other crosses performed. Each pairwise combination produced some viable progeny that grew into flowering plants.

The flowering $F_1$ plants were assessed and those that had desirable characteristics (such as high pollen fertility, certain flower colours or flower colour patterns, compact habits, etc.) were used as male parents for crossing to aneu-tetraploid *Argyranthemum* female parents. The aim was to further increase the diversity of aneu-triploid progeny and incorporate new genes and genetic combinations into the progeny. For example, *Glebionis segetum* does not produce many progeny when crossed to aneu-tetraploid *Argyranthemum* female parents. By crossing *Glebionis segetum* with *Ismelia versicolor*, developing an $F_1$ hybrid plant and using the $F_1$ hybrid plant as a male parent in crossing with an aneu-tetraploid *Argyranthemum* female parent, genes from *Glebionis segetum* were incorporated into the aneu-triploid progeny. This type of hybridization is called a bridging cross.

$F_1$ hybrids between *Ismelia versicolor*×*Glebionis coronaria* and *Glebionis coronaria*×*Ismelia versicolor* have been previously reported by Chaudhuri B. K., Chaudhuri S. K. Basak, S. L. and Dana, S, *Cytogenetics of a cross between two species of annual Chrysanthemum*, Cytologia 41:111-121 (1976). These authors also reported developing $F_2$ hybrids by intercrossing the $F_1$ hybrids. Boase, M, Miller, R and Deroles, S, *Chrysanthemum systematic, genetics and breeding*, Plant Breeding Reviews no. 14, p 321-361, John Wiley and Sons (1997) mention *I. versicolor* and *G. coronaria* can hybridise. Dowrick, G. and El-Bayoumi, A, *Nucleic acid content and chromosome morphology in Chrysanthemum*, Genetic Research Cambridge 13: 241-250 (1969) investigated the DNA content of a hybrid between *G. segetum* and *G. coronaria*. Tables 5A, 5B, and 5C below show the results of interspecies crossings conducted during years 2000-2012 in Yellow Rock, NSW, Australia. Female parent lines are shown in the first column and male parent lines in the top row of each table, listed by their plant identification numbers. Embryos were rescued between 14 and 21 days after pollination. Table 5A shows the number of capitula pollinated for each cross. Table 5B shows the number of embryos rescued. Table 5C shows the number of embryos that germinated and were planted into pots in the greenhouse. DU indicates that data is not available.

TABLE 5A

Number of *I. versicolor* and *Glebionis* sp. female parents pollinated with pollen from *I. versicolor* and *Glebionis* sp. male parents

| | | Ismelia versicolor | | | | | | | | Glebionis segetum | | | | | Glebionis coronaria | | | |
|---|---|---|---|---|---|---|---|---|---|---|---|---|---|---|---|---|---|---|
| | | CC2 | CC3 | CC5 | 08-80 | 08-81 | 08-86 | 10-12 | 10-17 | CS1 | CS2 | 08-83 | 08-89 | 09-27 | 10-18 | 10-20 | CCo1 | CCo2 | CCo3 |
| Ismelia versicolor | CC2 | 0 | 0 | 0 | 0 | 0 | 0 | 0 | 0 | 1 | 1 | 0 | 0 | 0 | 0 | 0 | 1 | 1 | 1 |
| | CC3 | 0 | 0 | 0 | 0 | 0 | 0 | 0 | 0 | 0 | 0 | 0 | 0 | 0 | 0 | 0 | 1 | 1 | 1 |
| | CC4 | 0 | 0 | 0 | 0 | 0 | 0 | 0 | 0 | 0 | 0 | 0 | 0 | 0 | 0 | 0 | 1 | 1 | 1 |
| | CC5 | 0 | 0 | 0 | 0 | 0 | 0 | 0 | 0 | 1 | 1 | 0 | 0 | 0 | 0 | 0 | 1 | 1 | 1 |
| | 08-80 | 0 | 0 | 0 | 0 | 0 | 0 | 0 | 0 | 0 | 0 | 2 | 2 | 0 | 2 | 0 | 0 | 0 | 0 |
| | 08-81 | 0 | 0 | 0 | 0 | 0 | 0 | 0 | 0 | 0 | 0 | 2 | 2 | 0 | 2 | 0 | 0 | 0 | 0 |
| | 08-82 | 0 | 0 | 0 | 0 | 0 | 0 | 0 | 0 | 0 | 0 | 0 | 2 | 0 | 2 | 0 | 0 | 0 | 0 |
| | 08-86 | 0 | 0 | 0 | 0 | 0 | 0 | 0 | 0 | 0 | 0 | 0 | 0 | 0 | 0 | 0 | 0 | 0 | 0 |

TABLE 5A-continued

Number of *I. versicolor* and *Glebionis* sp. female parents pollinated with pollen from *I. versicolor* and *Glebionis* sp. male parents

| | | *Ismelia versicolor* | | | | | | | | *Glebionis segetum* | | | | | *Glebionis coronaria* | | | | |
|---|---|---|---|---|---|---|---|---|---|---|---|---|---|---|---|---|---|---|---|
| | | CC2 | CC3 | CC5 | 08-80 | 08-81 | 08-86 | 10-12 | 10-17 | CS1 | CS2 | 08-83 | 08-89 | 09-27 | 10-18 | 10-20 | CCo1 | CCo2 | CCo3 |
| | 10-12 | 0 | 0 | 0 | 0 | 0 | 0 | 0 | 0 | 0 | 0 | 2 | 2 | 0 | 0 | 2 | 0 | 0 | 0 |
| | 10-17 | 0 | 0 | 0 | 0 | 0 | 0 | 0 | 0 | 0 | 0 | 2 | 2 | 0 | 0 | 2 | 0 | 0 | 0 |
| *Glebionis* | CS1 | 1 | 1 | 1 | 0 | 0 | 0 | 0 | 0 | 0 | 0 | 0 | 0 | 0 | 0 | 0 | 1 | 1 | 1 |
| *segetum* | CS2 | 1 | 1 | 1 | 0 | 0 | 0 | 0 | 0 | 0 | 0 | 0 | 0 | 0 | 0 | 0 | 1 | 1 | 1 |
| | 08-83 | 0 | 0 | 0 | 2 | 2 | 0 | 2 | 2 | 0 | 0 | 0 | 0 | 0 | 0 | 0 | 0 | 0 | 0 |
| | 08-89 | 0 | 0 | 0 | 2 | 2 | 0 | 2 | 2 | 0 | 0 | 0 | 0 | 0 | 0 | 0 | 0 | 0 | 0 |
| | 09-27 | 0 | 0 | 0 | 2 | 2 | 0 | 2 | 2 | 0 | 0 | 0 | 0 | 0 | 3 | 0 | 0 | 0 | 0 |
| | 09-28 | 0 | 0 | 0 | 2 | 2 | 0 | 2 | 2 | 0 | 0 | 0 | 0 | 0 | 0 | 0 | 0 | 0 | 0 |
| *Glebionis* | 10-18 | 0 | 0 | 0 | 1 | 0 | 1 | 0 | 0 | 0 | 0 | 0 | 0 | 3 | 0 | 0 | 0 | 0 | 0 |
| *coronaria* | 10-19 | 0 | 0 | 0 | 1 | 0 | 1 | 0 | 0 | 0 | 0 | 0 | 0 | 0 | 0 | 0 | 0 | 0 | 0 |
| | 10-20 | 0 | 0 | 0 | 0 | 0 | 1 | 3 | 0 | 0 | 0 | 0 | 2 | 0 | 0 | 0 | 0 | 0 | 0 |
| | 10-21 | 0 | 0 | 0 | 0 | 1 | 1 | 0 | 0 | 0 | 0 | 0 | 0 | 0 | 0 | 0 | 0 | 0 | 0 |
| | CCo1 | 0 | 0 | 0 | 0 | 0 | 0 | 0 | 0 | 1 | 0 | 0 | 0 | 0 | 0 | 0 | 0 | 0 | 0 |
| | CCo2 | 0 | 0 | 0 | 0 | 0 | 0 | 0 | 0 | 1 | 0 | 0 | 0 | 0 | 0 | 0 | 0 | 0 | 0 |
| | CCo3 | 0 | 0 | 0 | 0 | 0 | 0 | 0 | 0 | 1 | 0 | 0 | 0 | 0 | 0 | 0 | 0 | 0 | 0 |

As shown in Table 5A above, for example, two capitula were pollinated in a cross between the female *Glebionis segetum* plant, 08-89, and the male *Ismelia versicolor* plant, 08-80 (row 16, column 6).

TABLE 5B

Number of embryos rescued from *I. versicolor* and *Glebionis* sp. female parents pollinated with pollen from *I. versicolor* and *Glebionis* sp. male parents.

| | | *Ismelia versicolor* | | | | | | | | *Glebionis segetum* | | | | | *Glebionis coronaria* | | | | |
|---|---|---|---|---|---|---|---|---|---|---|---|---|---|---|---|---|---|---|---|
| | | CC2 | CC3 | CC5 | 08-80 | 08-81 | 08-86 | 10-12 | 10-17 | CS1 | CS2 | 08-83 | 08-89 | 09-27 | 10-18 | 10-20 | CCo1 | CCo2 | CCo3 |
| *Ismelia* | CC2 | 0 | 0 | 0 | 0 | 0 | 0 | 0 | 0 | 0 | 0 | 0 | 0 | 0 | 0 | 0 | 0 | 47 | 1 |
| *versicolor* | CC3 | 0 | 0 | 0 | 0 | 0 | 0 | 0 | 0 | 0 | 0 | 0 | 0 | 0 | 0 | 0 | 0 | 20 | 0 |
| | CC4 | 0 | 0 | 0 | 0 | 0 | 0 | 0 | 0 | 0 | 0 | 0 | 0 | 0 | 0 | 0 | 0 | 0 | 0 |
| | CC5 | 0 | 0 | 0 | 0 | 0 | 0 | 0 | 0 | 0 | 1 | 0 | 0 | 0 | 0 | 0 | 0 | 13 | 20 |
| | 08-80 | 0 | 0 | 0 | 0 | 0 | 0 | 0 | 0 | 0 | 0 | 20 | 5 | 0 | 0 | 53 | 0 | 0 | 0 |
| | 08-81 | 0 | 0 | 0 | 0 | 0 | 0 | 0 | 0 | 0 | 0 | 0 | 15 | 0 | 0 | 55 | 0 | 0 | 0 |
| | 08-82 | 0 | 0 | 0 | 0 | 0 | 0 | 0 | 0 | 0 | 0 | 0 | 25 | 0 | 0 | 40 | 0 | 0 | 0 |
| | 08-86 | 0 | 0 | 0 | 0 | 0 | 0 | 0 | 0 | 0 | 0 | 0 | 0 | 0 | 0 | 0 | 0 | 0 | 0 |
| | 10-12 | 0 | 0 | 0 | 0 | 0 | 0 | 0 | 0 | 0 | 0 | 0 | 18 | 0 | 0 | 51 | 0 | 0 | 0 |
| | 10-17 | 0 | 0 | 0 | 0 | 0 | 0 | 0 | 0 | 0 | 0 | 2 | 0 | 0 | 0 | 6 | 0 | 0 | 0 |
| *Glebionis* | CS1 | 0 | 4 | 0 | 0 | 0 | 0 | 0 | 0 | 0 | 0 | 0 | 0 | 0 | 0 | 0 | 0 | 0 | 12 |
| *segetum* | CS2 | 0 | 0 | 2 | 0 | 0 | 0 | 0 | 0 | 0 | 0 | 0 | 0 | 0 | 0 | 0 | 0 | 11 | 0 |
| | 08-83 | 0 | 0 | 0 | 1 | 2 | 0 | 1 | 9 | 0 | 0 | 0 | 0 | 0 | 0 | 0 | 0 | 0 | 0 |
| | 08-89 | 0 | 0 | 0 | 14 | 27 | 0 | 29 | 29 | 0 | 0 | 0 | 0 | 0 | 0 | 0 | 0 | 0 | 0 |
| | 09-27 | 0 | 0 | 0 | 8 | 33 | 0 | 20 | 29 | 0 | 0 | 0 | 0 | 0 | 66 | 0 | 0 | 0 | 0 |
| | 09-28 | 0 | 0 | 0 | 2 | 19 | 0 | 1 | 0 | 0 | 0 | 0 | 0 | 0 | 0 | 0 | 0 | 0 | 0 |
| *Glebionis* | 10-18 | 0 | 0 | 0 | 2 | 0 | 6 | 0 | 0 | 0 | 0 | 0 | 0 | 10 | 0 | 0 | 0 | 0 | 0 |
| *coronaria* | 10-19 | 0 | 0 | 0 | 1 | 0 | 0 | 0 | 0 | 0 | 0 | 0 | 0 | 0 | 0 | 0 | 0 | 0 | 0 |
| | 10-20 | 0 | 0 | 0 | 0 | 0 | 0 | 0 | 0 | 0 | 0 | 0 | 0 | 0 | 0 | 0 | 0 | 0 | 0 |
| | 10-21 | 0 | 0 | 0 | 0 | 0 | 0 | 0 | 0 | 0 | 0 | 0 | 0 | 0 | 0 | 0 | 0 | 0 | 0 |
| | CCo1 | 0 | 0 | 0 | 0 | 0 | 0 | 0 | 0 | DU | 0 | 0 | 0 | 0 | 0 | 0 | 0 | 0 | 0 |
| | CCo2 | 0 | 0 | 0 | 0 | 0 | 0 | 0 | 0 | DU | 0 | 0 | 0 | 0 | 0 | 0 | 0 | 0 | 0 |
| | CCo3 | 0 | 0 | 0 | 0 | 0 | 0 | 0 | 0 | DU | 0 | 0 | 0 | 0 | 0 | 0 | 0 | 0 | 0 |

As shown in Table 5B above, from the two pollinations of female *Glebionis segetum* plant, 08-89, and the male *Ismelia versicolor* plant, 08-80, 14 embryos were rescued (row 16, column 6).

TABLE 5C

Number of embryos that germinated and were grown into plants from *I. versicolor* and *Glebionis* sp. female parents pollinated with pollen from *I. versicolor* and *Glebionis* sp. male parents.

|  |  | *Ismelia versicolor* | | | | | | | | *Glebionis segetum* | | | | | *Glebionis coronaria* | | | | |
| --- | --- | --- | --- | --- | --- | --- | --- | --- | --- | --- | --- | --- | --- | --- | --- | --- | --- | --- | --- |
|  |  | CC2 | CC3 | CC5 | 08-80 | 08-81 | 08-86 | 10-12 | 10-17 | CS1 | CS2 | 08-83 | 08-89 | 09-27 | 10-18 | 10-20 | CCo1 | CCo2 | CCo3 |
| *Ismelia* | CC2 | 0 | 0 | 0 | 0 | 0 | 0 | 0 | 0 | 0 | 0 | 0 | 0 | 0 | 0 | 0 | 0 | DU | DU |
| *versicolor* | CC3 | 0 | 0 | 0 | 0 | 0 | 0 | 0 | 0 | 0 | 0 | 0 | 0 | 0 | 0 | 0 | 0 | DU | 0 |
|  | CC4 | 0 | 0 | 0 | 0 | 0 | 0 | 0 | 0 | 0 | 0 | 0 | 0 | 0 | 0 | 0 | 0 | 0 | 0 |
|  | CC5 | 0 | 0 | 0 | 0 | 0 | 0 | 0 | 0 | 0 | DU | 0 | 0 | 0 | 0 | 0 | 0 | DU | DU |
|  | 08-80 | 0 | 0 | 0 | 0 | 0 | 0 | 0 | 0 | 0 | 0 | 0 | 3 | 0 | 0 | 37 | 0 | 0 | 0 |
|  | 08-81 | 0 | 0 | 0 | 0 | 0 | 0 | 0 | 0 | 0 | 0 | 0 | 3 | 0 | 0 | 41 | 0 | 0 | 0 |
|  | 08-82 | 0 | 0 | 0 | 0 | 0 | 0 | 0 | 0 | 0 | 0 | 0 | 18 | 0 | 0 | 28 | 0 | 0 | 0 |
|  | 08-86 | 0 | 0 | 0 | 0 | 0 | 0 | 0 | 0 | 0 | 0 | 0 | 0 | 0 | 0 | 0 | 0 | 0 | 0 |
|  | 10-12 | 0 | 0 | 0 | 0 | 0 | 0 | 0 | 0 | 0 | 0 | 0 | 9 | 0 | 0 | 43 | 0 | 0 | 0 |
|  | 10-17 | 0 | 0 | 0 | 0 | 0 | 0 | 0 | 0 | 0 | 0 | 1 | 0 | 0 | 0 | 5 | 0 | 0 | 0 |
| *Glebionis* | CS1 | 0 | DU | 0 | 0 | 0 | 0 | 0 | 0 | 0 | 0 | 0 | 0 | 0 | 0 | 0 | 0 | 0 | DU |
| *segetum* | CS2 | 0 | 0 | DU | 0 | 0 | 0 | 0 | 0 | 0 | 0 | 0 | 0 | 0 | 0 | 0 | 0 | DU | 0 |
|  | 08-83 | 0 | 0 | 0 | 1 | 2 | 0 | 0 | 7 | 0 | 0 | 0 | 0 | 0 | 0 | 0 | 0 | 0 | 0 |
|  | 08-89 | 0 | 0 | 0 | 10 | 23 | 0 | 27 | 26 | 0 | 0 | 0 | 0 | 0 | 0 | 0 | 0 | 0 | 0 |
|  | 09-27 | 0 | 0 | 0 | 4 | 0 | 0 | 6 | 15 | 0 | 0 | 0 | 0 | 0 | 56 | 0 | 0 | 0 | 0 |
|  | 09-28 | 0 | 0 | 0 | 0 | 10 | 0 | 0 | 0 | 0 | 0 | 0 | 0 | 0 | 0 | 0 | 0 | 0 | 0 |
| *Glebionis* | 10-18 | 0 | 0 | 0 | 1 | 0 | 4 | 0 | 0 | 0 | 0 | 0 | 0 | 7 | 0 | 0 | 0 | 0 | 0 |
| *coronaria* | 10-19 | 0 | 0 | 0 | 1 | 0 | 0 | 0 | 0 | 0 | 0 | 0 | 0 | 0 | 0 | 0 | 0 | 0 | 0 |
|  | 10-20 | 0 | 0 | 0 | 0 | 0 | 0 | 0 | 0 | 0 | 0 | 0 | 0 | 0 | 0 | 0 | 0 | 0 | 0 |
|  | 10-21 | 0 | 0 | 0 | 0 | 0 | 0 | 0 | 0 | 0 | 0 | 0 | 0 | 0 | 0 | 0 | 0 | 0 | 0 |
|  | CCo1 | 0 | 0 | 0 | 0 | 0 | 0 | 0 | 0 | 0 | 0 | 0 | 0 | 0 | 0 | 0 | 0 | 0 | 0 |
|  | CCo2 | 0 | 0 | 0 | 0 | 0 | 0 | 0 | 0 | 0 | 0 | 0 | 0 | 0 | 0 | 0 | 0 | 0 | 0 |
|  | CCo3 | 0 | 0 | 0 | 0 | 0 | 0 | 0 | 0 | 0 | 0 | 0 | 0 | 0 | 0 | 0 | 0 | 0 | 0 |

As shown in Table 5C above, of the 14 embryos rescued (Table 5B) from the two pollinations of female *Glebionis segetum* plant, 08-89, and the male *Ismelia versicolor* plant, 08-80, 10 embryos germinated and were grown into plants in the greenhouse (row 16, column 6).

Example 7

Bridging Crosses Using Aneu-Tetraploid *Argyranthemum* as Female Parents and Various Male *Glebionis* sp.×*I. versicolor* Hybrid Male Parents Following on from the development of interspecific hybrid progeny from crosses between *I. versicolor* and *Glebionis* sp., crosses were performed between aneu-tetraploid Argyranthemums as female parents and various *Glebionis* sp.×*I. versicolor* hybrid male parents. The aneu-tetraploid female parents were placed into groups based on the diploid parent they were derived from and 5 capitula were pollinated within each group for each male parent listed. Two male parents were selected for each male parent cross combination. In Tables 6A, B and C below, the left side column represents aneu-tetraploid *Argyranthemum* female parents and the remaining 8 columns represent various *I. versicolor*×*Glebionis* sp. hybrid male parents in various combinations. Table 6A shows the number of capitula pollinated, Table 6B shows the number of embryos rescued from the cross pollinations, and Table 6C shows the number of hybrid bridging cross plants developed.

TABLE 6A

Number of capitula pollinated using aneu-tetraploid *Argyranthemum* as female parents and various male *Glebionis* sp. × *I. versicolor* hybrid male parents

| Accn Nos | *versicolor* × *segetum* | | *versicolor* × *coronaria* | | *segetum* × *versicolor* | | *coronaria* × *versicolor* | |
| --- | --- | --- | --- | --- | --- | --- | --- | --- |
|  | 11-172 | 11-203 | 11-176 | 11-179 | 11-166 | 11-167 | 11-184 | 11-186 |
| 09-3 | 5 | 5 | 5 | 5 | 5 | 5 | 5 | 5 |
| 09-4 |  |  |  |  |  |  |  |  |
| 09-5 |  |  |  |  |  |  |  |  |
| 09-6 |  |  |  |  |  |  |  |  |
| 09-8 | 5 | 5 | 5 | 5 | 5 | 5 | 5 | 5 |
| 09-10 |  |  |  |  |  |  |  |  |
| 09-12 |  |  |  |  |  |  |  |  |
| 08-119 | 5 | 5 | 5 | 5 | 5 | 5 | 5 | 5 |
| 08-124 |  |  |  |  |  |  |  |  |
| 09-20 |  |  |  |  |  |  |  |  |
| 09-21 |  |  |  |  |  |  |  |  |
| 10-114 | 5 | 5 | 5 | 5 | 5 | 5 | 5 | 5 |
| 10-115 |  |  |  |  |  |  |  |  |
| 10-117 |  |  |  |  |  |  |  |  |
| 10-121 |  |  |  |  |  |  |  |  |

TABLE 6A-continued

Number of capitula pollinated using aneu-tetraploid *Argyranthemum* as female parents and various male *Glebionis* sp. × *I. versicolor* hybrid male parents

| Accn Nos | versicolor × segetum | | versicolor × coronaria | | segetum × versicolor | | coronaria × versicolor | |
|---|---|---|---|---|---|---|---|---|
| | 11-172 | 11-203 | 11-176 | 11-179 | 11-166 | 11-167 | 11-184 | 11-186 |
| 10-105 10-106 10-108 10-110 10-112 | 5 | 5 | 5 | 5 | 5 | 5 | 5 | 5 |

15

TABLE 6B

Number of embryos rescued from capitula pollinated using aneu-tetraploid *Argyranthemum* as female parents and various male *Glebionis* sp. × *I. versicolor* hybrid male parents.

| Accn Nos | versicolor × segetum | | versicolor × coronaria | | segetum × versicolor | | coronaria × versicolor | |
|---|---|---|---|---|---|---|---|---|
| | 11-172 | 11-203 | 11-176 | 11-179 | 11-166 | 11-167 | 11-184 | 11-186 |
| 09-3 09-4 09-5 09-6 | 0 | 0 | 0 | 17 | 0 | 0 | 0 | 0 |
| 09-8 09-10 09-12 | 38 | 13 | 16 | 32 | 0 | 4 | 0 | 0 |
| 08-119 08-124 09-20 09-21 | 0 | 0 | 0 | 0 | 0 | 0 | 0 | 0 |
| 10-114 10-115 10-117 10-121 | 0 | 0 | 0 | 1 | 0 | 0 | 0 | 0 |
| 10-105 10-106 10-108 10-110 10-112 | 2 | 1 | 33 | 59 | 0 | 4 | 0 | 1 |

As shown in Table 6B, the total number of embryos rescued from the cross pollinations performed was 221.

TABLE 6C

Number of plants grown from capitula pollinated using aneu-tetraploid *Argyranthemum* as female parents and various male *Glebionis* sp. × *I. versicolor* hybrid male parents

| Accn Nos | versicolor × segetum | | versicolor × coronaria | | segetum × versicolor | | coronaria × versicolor | |
|---|---|---|---|---|---|---|---|---|
| | 11-172 | 11-203 | 11-176 | 11-179 | 11-166 | 11-167 | 11-184 | 11-186 |
| 09-3 09-4 09-5 09-6 | 0 | 0 | 0 | 8 | 0 | 0 | 0 | 0 |
| 09-8 09-10 09-12 | 29 | 12 | 13 | 24 | 0 | 0 | 0 | 0 |
| 08-119 08-124 09-20 09-21 | 0 | 0 | 0 | 0 | 0 | 0 | 0 | 0 |

TABLE 6C-continued

Number of plants grown from capitula pollinated using aneu-tetraploid
*Argyranthemum* as female parents and various male *Glebionis* sp. × *I. versicolor*
hybrid male parents

| | versicolor × segetum | | versicolor × coronaria | | segetum × versicolor | | coronaria × versicolor | |
|---|---|---|---|---|---|---|---|---|
| Accn Nos | 11-172 | 11-203 | 11-176 | 11-179 | 11-166 | 11-167 | 11-184 | 11-186 |
| 10-114 | 0 | 0 | 0 | 0 | 0 | 0 | 0 | 0 |
| 10-115 | | | | | | | | |
| 10-117 | | | | | | | | |
| 10-121 | | | | | | | | |
| 10-105 | 2 | 0 | 11 | 31 | 0 | 2 | 0 | 0 |
| 10-106 | | | | | | | | |
| 10-108 | | | | | | | | |
| 10-110 | | | | | | | | |
| 10-112 | | | | | | | | |

As shown in Table 6C, the total number of hybrid bridging cross plants developed was 132.

The plants derived from the work performed in Tables 6A, B, and C allowed the integration of several combined characteristics from *Argyranthemum*, *Glebionis* sp. and *I. versicolor*. It can be appreciated by one skilled in the art that further repetition of crosses and fine tuning of the parental combinations could yield increased numbers of progeny and plants in all cross combinations.

Example 8

Method of Hybridization of an *Ismelia versicolor* Plant with an *Argyranthemum* Aneu-Tetraploid Plant Another aspect of the present invention involved crossing a plant from the group consisting of *Ismelia versicolor* with an aneu-tetraploid plant of the genus *Argyranthemum*. The female *I. versicolor* plants were selected for desired traits such as flower colour, flower banding pattern, ease of growth and propagation, branching intensity, earliness to flower and male and female fertility. Pollen was then removed from a selected aneu-tetraploid *Argyranthemum* plant being used as a male parent. Pollen was applied using a small brush onto a capitulum of the *I. versicolor* female plant when the *I. versicolor* capitulum was receptive. Emasculation of the *I. versicolor* capitulum was not performed. The capitulum from the *I. versicolor* plant pollinated with pollen from the aneu-tetraploid *Argyranthemum* plant was then harvested after two to three weeks and the florets were removed. Aseptic technique was then applied to each floret. Florets were preferably placed intact into a vessel with 1% sodium hypochlorite added to cover the material, followed by one drop of Tween 20 detergent. The vessel was closed with a lid and shaken once per minute for five minutes. The vessel was then emptied and the florets rinsed three times in distilled autoclaved water. Florets were then removed and individually dissected. Any developing seed coat and ovary wall tissue was then removed to reveal the ovule. The embryo was then removed from the ovule and placed onto appropriate embryo rescue media in a petri dish. The media preferably contained Murashige and Skoog (1962) salts (Murashige, T. and Skoog, F, A revised medium for rapid growth and bio assays with tobacco tissue cultures, Physiologia Plantarum, 15:473-497 (1962)) at half the recommended rate (i.e., 2.21 g/L), 1% activated charcoal, 20 g/L sucrose, and 0.7% agar. Media was adjusted to pH 5.8 prior to autoclaving at 1 kg/m$^2$ at 121° C. for seventeen minutes. Petri dishes with dissected embryos were sealed with parafilm and placed into a growth chamber maintained under fluorescent lights for sixteen hours per day at a continuous temperature of 25° C. After two to four weeks, the germinated embryos were transplanted to a greenhouse environment where their development was promoted into mature plants following conventional nursery practice suitable for growth of *Argyranthemum* plants (e.g., Hamrick, D. (Ed), (2003)). For example, the germinated embryos were transplanted into a seed raising mixture that included fertilizer, and kept moist and shaded. The germinated embryos were subsequently transplanted into larger pots with conventional potting media and high light intensity, and allowed to grow and flower. Desirable putative $F_1$ hybrid plants were then selected and cuttings were taken.

Example 9

Method of Hybridization of a *Glebionis coronaria* Plant with an Aneu-Tetraploid *Argyranthemum* Plant Another aspect of the present invention involves the steps of crossing a plant from the group consisting of *Glebionis coronaria* with an aneu-tetraploid plant of the genus *Argyranthemum*. The female *G. coronaria* plants were selected for desired traits such as flower colour, flower banding pattern, ease of growth and propagation, branching intensity, earliness to flower and male and female fertility. Pollen was removed from a selected aneu-tetraploid *Argyranthemum* plant being used as a male parent. Pollen was applied using a small brush onto a capitulum of the *G. coronaria* female plant when the *G. coronaria* capitulum was receptive. Emasculation of the *G. coronaria* capitulum was performed. The capitulum from the *G. coronaria* plant pollinated with pollen from the aneu-tetraploid *Argyranthemum* plant was then harvested after two to three weeks and the florets were removed. Aseptic technique was then applied to each floret. Florets were preferably placed intact into a vessel with 1% sodium hypochlorite added to cover the material, followed by one drop of Tween 20 detergent. The vessel was closed with a lid and shaken once per minute for five minutes. The vessel was then emptied and the florets rinsed three times in distilled autoclaved water. Florets were then removed and individually dissected. Any developing seed coat and ovary wall tissue was then removed to reveal the ovule. The embryo was then removed from the ovule and placed onto appropriate embryo rescue media in a petri dish. The media preferably contained Murashige and Skoog (1962) salts at half the recommended rate (i.e., 2.21 g/L), 1% activated charcoal, 20 g/L sucrose, and 0.7% agar. Media was adjusted to pH 5.8 prior to autoclaving at 1 kg/m² at 121° C. for 17 minutes. Petri dishes with dissected embryos were sealed with parafilm and placed into a growth chamber maintained under fluorescent lights for 16 hours per day at a continuous temperature of 25° C. After two to four weeks, the germinated embryos were transplanted to a greenhouse environment where their development was promoted into mature plants following conventional nursery practice suitable for growth of *Argyranthemum* plants (e.g., Hamrick, D. (Ed), (2003)). For example, the germinated embryos were transplanted into a seed raising mixture that included fertilizer, and kept moist and shaded. The germinated embryos were subsequently transplanted into larger pots with conventional potting media and high light intensity, and allowed to grow and flower. Desirable putative $F_1$ hybrid plants were then selected and cuttings were taken.

Example 10

Method of Hybridization of a *Glebionis segetum* Plant with an Aneu-Tetraplod *Argyranthemum* Plant Another aspect of the present invention involved the steps of crossing a plant from the group consisting of *Glebionis segetum* with an aneu-tetraploid plant of the genus *Argyranthemum*. The female *G. segetum* plants were selected for desired traits such as flower colour, ease of growth and propagation, branching intensity, earliness to flower and male and female fertility. Pollen was removed from a selected aneu-tetraploid *Argyranthemum* plant being used as a male parent. Pollen was applied using a small brush onto a capitulum of the *G. segetum* female plant when the *G. segetum* capitulum was receptive. Emasculation of the *G. segetum* capitulum was not performed. The capitulum from the *G. segetum* plant pollinated with pollen from the aneu-tetraploid *Argyranthemum* plant was then harvested after two to three weeks and the florets were removed. Aseptic technique was then applied to each floret. Florets were preferably placed intact into a vessel with 1% sodium hypochlorite added to cover the material, followed by one drop of Tween 20 detergent. The vessel was closed with a lid and shaken once per minute for five minutes. The vessel was then emptied and the florets rinsed three times in distilled autoclaved water. Florets were then removed and individually dissected. Any developing seed coat and ovary wall tissue was then removed to reveal the ovule. The embryo was then removed from the ovule and placed onto appropriate embryo rescue media in a petri dish. The media preferably contained Murashige and Skoog (1962) salts at half the recommended rate (i.e., 2.21 g/L), 1% activated charcoal, 20 g/L sucrose, and 0.7% agar. Media was adjusted to pH 5.8 prior to autoclaving at 1 kg/m² at 121° C. for 17 minutes. Petri dishes with dissected embryos were sealed with parafilm and placed into a growth chamber maintained under fluorescent lights for 16 hours per day at a continuous temperature of 25° C. After two to four weeks, the germinated embryos were transplanted to a greenhouse environment where their development was promoted into mature plants following conventional nursery practice suitable for growth of *Argyranthemum* plants (e.g., Hamrick, D. (Ed), (2003)). For example, the germinated embryos were transplanted into a seed raising mixture that included fertilizer, and kept moist and shaded. The germinated embryos were subsequently transplanted into larger pots with conventional potting media and high light intensity, and allowed to grow and flower. Desirable putative $F_1$ hybrid plants were then selected and cuttings were taken.

Example 11

Intergeneric Crossing Using *I. versicolor* and *Glebionis* sp. as Female Parents and *Argyranthemum* Aneu-Tetraploids as Male Parents Crosses were performed using *I. versicolor* and *Glebionis* sp. as female parents and *Argyranthemum* aneu-tetraploids as male parents, following the methods described previously. Table 7A shows the number of capitula pollinated using *I. versicolor* and *Glebionis* sp. as female parents and *Argyranthemum* aneu-tetraploids as male parents.

TABLE 7A

Number of capitula pollinated from intergeneric crossing using *I. versicolor* and *Glebionis* sp. as female parents and *Argyranthemum* aneu-tetraploids as male parents

| | | Aneu-tetraploid *Argyranthemum* male parents | | | | | |
| --- | --- | --- | --- | --- | --- | --- | --- |
| | | 09-5 | 09-6 | 09-10 | 09-12 | 09-21 | 11-455 | 11-458 |
| *I. versicolor* | 08-80 | 5 | 3 | 3 | 5 | 0 | 3 | 4 |
| *G. coronaria* | 10-18 | 3 | 3 | 1 | 6 | 2 | 2 | 3 |
| *G. segetum* | 09-27 | 3 | 3 | 3 | 2 | 2 | 2 | 3 |

As shown in Table 7A, a total of 61 capitula were pollinated using *I. versicolor* and *Glebionis* sp. as female parents and *Argyranthemum* aneu-tetraploids as male parents.

Table 7B shows the number of embryos were rescued from pollinations pollinated using *I. versicolor* and *Glebionis* sp. as female parents and *Argyranthemum* aneu-tetraploids as male parents.

TABLE 7B

Number of embryos rescued from intergeneric crossing using *I. versicolor* and *Glebionis* sp. as female parents and *Argyranthemum* aneu-tetraploids as male parents

| | | Aneu-tetraploid *Argyranthemum* male parents | | | | | |
| --- | --- | --- | --- | --- | --- | --- | --- |
| | | 09-5 | 09-6 | 09-10 | 09-12 | 09-21 | 11-455 | 11-458 |
| *I. versicolor* | 08-80 | 32 | 0 | 4 | 25 | 0 | 23 | 39 |
| *G. coronaria* | 10-18 | 38 | 24 | 0 | 55 | 42 | 39 | 18 |
| *G. segetum* | 09-27 | 0 | 0 | 0 | 0 | 1 | 0 | 1 |

As shown in Table 7B, a total of 341 embryos were rescued from pollinations pollinated using *I. versicolor* and *Glebionis* sp. as female parents and *Argyranthemum* aneu-tetraploids as male parents.

Table 7C shows the number of hybrids and selfs developed from pollinations using *I. versicolor* and *Glebionis* sp. as female parents and *Argyranthemum* aneu-tetraploids as male parents.

TABLE 7C

Number of embryos grown into plants and the number of hybrid and self plants as determined by morphology from pollinations using *I. versicolor* and *Glebionis* sp. as female parents and *Argyranthemum* aneu-tetraploids as male parents

| | | Aneu-tetraploid *Argyranthemum* male parents | | | | | | |
|---|---|---|---|---|---|---|---|---|
| | | 09-5 | 09-6 | 09-10 | 09-12 | 09-21 | 11-455 | 11-458 | Total |
| *I. versicolor* | 08-80 | 8 | 0 | 4 | 8 | 0 | 7 | 11 | 14 hybrids, 24 selfs |
| *G. coronaria* | 10-18 | 33 | 11 | 0 | 45 | 19 | 36 | 10 | 22 hybrids, 142 selfs |
| *G. segetum* | 09-27 | 0 | 0 | 0 | 0 | 1 | 0 | 0 | 1 hybrid |

As shown in Table 7C, a total of 37 hybrids and 166 selfs were developed from pollinations using *I. versicolor* and *Glebionis* sp. as female parents and *Argyranthemum* aneu-tetraploids as male parents.

The work performed in Tables 7A, B, and C demonstrated that using plants from the group *I. versicolor* and *Glebionis* sp. as female parents crossed with male aneu-tetraploid *Argyranthemum* plants could yield hybrid progeny as well as self progeny.

Table 7D shows the chromosome counts of selected intergeneric hybrid plants shown in Table 7C.

TABLE 7D

Chromosome counts of selected intergeneric hybrid plants shown in Table 7C

| Plant No. | Pedigree | 2n |
|---|---|---|
| 12-125 | *I. versicolour* × aneu-tetraploid *Argyranthemum* | 18 |
| 12-126 | *I. versicolour* × aneu-tetraploid *Argyranthemum* | 18 |
| 12-1 | *G. coronaria* × aneu-tetraploid *Argyranthemum* | 25, 27 |
| 12-2 | *G. coronaria* × aneu-tetraploid *Argyranthemum* | 23, 24, 27 |
| 12-127 | *G. coronaria* × aneu-tetraploid *Argyranthemum* | 18 |
| 12-123 | *G. segetum* × aneu-tetraploid *Argyranthemum* | 14, 15, 16, 18 |

As shown in Table 7D, chromosome counts were expected to be approximately 2n=27 for all hybrid plants developed, but surprisingly there was a wide variation in the numbers observed.

Example 12

Intergeneric Crossing Using *I. versicolor* and *Glebionis* sp. as Female Parents and *Argyranthemum* Diploids as Male Parents Because the crossing results shown in Example 11 were promising, it was decided to attempt similar crosses, using *I. versicolor* and *Glebionis* sp. plants as female parents and *Argyranthemum* diploid plants as male parents. Table 8A shows the number of capitula pollinated using *I. versicolor* and *Glebionis* sp. as female parents with three *Argyranthemum* diploid parents.

TABLE 8A

Number of pollinations performed between *I. versicolor* and *Glebionis* sp. as female parents and *Argyranthemum* diploids as male parents

| | | Diploid *Argyranthemum* male parents | | | |
|---|---|---|---|---|---|
| | | 04-36 | 04-79 | 04-92 | Total |
| *I. versicolor* | 08-80 | 3 | 3 | 3 | 9 |
| *G. coronaria* | 10-18 | 3 | 3 | 3 | 9 |
| *G. segetum* | 09-27 | 2 | 3 | 3 | 8 |
| Total | | | | | 26 |

As shown in Table 8A, a total of 26 capitula were pollinated using *I. versicolor* and *Glebionis* sp. as female parents with three *Argyranthemum* diploid parents.

Table 8B shows the number of embryos rescued from crosses using *I. versicolor* and *Glebionis* sp. as female parents with three *Argyranthemum* diploid parents.

TABLE 8B

Number of embryos rescued from crosses performed between *I. versicolor* and *Glebionis* sp. as female parents and *Argyranthemum* diploids as male parents.

| | | Diploid *Argyranthemum* male parents | | | |
|---|---|---|---|---|---|
| | | 04-36 | 04-79 | 04-92 | Total |
| *I. versicolor* | 08-80 | 17 | 6 | 45 | 68 |
| *G. coronaria* | 10-18 | 92 | 92 | 50 | 234 |
| *G. segetum* | 09-27 | 0 | 0 | 0 | 0 |
| | | | | | 604 |

As shown in Table 8B, a total of 604 embryos were rescued from crosses using *I. versicolor* and *Glebionis* sp. as female parents with three *Argyranthemum* diploid parents.

Table 8C shows the number of self plants and intergeneric hybrid plants developed from crosses using *I. versicolor* and *Glebionis* sp. as female parents with three *Argyranthemum* diploid parents.

TABLE 8C

Number of plants produced and their self or hybrid origin as determined by morphological characteristics, from crosses performed between *I. versicolor* and *Glebionis* sp. as female parents and *Argyranthemum* diploids as male parents.

| | | Diploid *Argyranthemum* male parents | | | |
|---|---|---|---|---|---|
| | | 04-36 | 04-79 | 04-92 | Total |
| *I. versicolor* | 08-80 | 7 | 5 | 16 | 6 hybrids, 22 selfs |
| *G. coronaria* | 10-18 | 84 | 58 | 39 | 7 hybrids, 174 selfs |
| *G. segetum* | 09-27 | 0 | 0 | 0 | |
| | | | | | 13 hybrids, 196 selfs |

As shown in Table 8C, a total of 196 self plants and 13 intergeneric hybrid plants were developed from crosses using *I. versicolor* and *Glebionis* sp. as female parents with three *Argyranthemum* diploid parents.

The work performed in Tables 8A, B, and C demonstrated that using plants from the group *I. versicolor* and *Glebionis* sp. as female parents crossed with male diploid *Argyranthemum* plants could yield hybrid progeny as well as self progeny.

Example 13

Using Aneu-Triploid Hybrids for Backcrossing

Almost all aneu-triploid hybrids developed from the aneu-tetraploid *Argyranthemum*×*Ismelia versicolor* cross were male sterile (possessing no pollen). However, occasionally, a plant was produced that possessed some pollen. Hybridisations were performed following the standard procedures previously described and two hybrid plants were developed from 18 pollinated capitula, as shown in Table 9. This result was surprising as it indicates some aneu-triploid intergeneric hybrid plants have the capacity as male parents for contributing to further breeding work, which is critical for the future development of new varieties.

Example 14

Introducing a Virus and Viroid to Modify Plant Phenotype

*Chrysanthemum* Virus B (CVB) and *Chrysanthemum* stunt viroid (CSVd) have been reported to infect *Argyranthemum* and numerous other species in the Asteraceae family. In *Argyranthemum*, infection with both CVB and CSVd either alone or combined, resulted in morphological changes to the infected plants, as reported by Rahman, M., *Virus and viroid studies in the marguerite daisy*. PhD thesis, University of Sydney, 2007. The morphological changes induced by these infective agents ranged from changes to flower colour, earliness of flowering and changes to plant habit. Several of the aneu-triploid hybrid plants (pedigree: aneu-tetraploid *Argyranthemum*×*Ismelia versicolor* and aneu-tetraploid *Argyranthemum*×*Glebionis coronaria*) developed by the methods described previously were selected to be grafted to an *Argyranthemum* plant infected with CSVd and CVB. The *Argyranthemum* plant infected with these two organisms was tested twice (after a 6 monthly interval), and both times confirmed infected with CSVd and CVB based on standard ELISA and PCR based techniques. Rooted cuttings of the aneu-triploid plants were approach grafted to rooted cuttings of the CSVd/CVB positive *Argyranthemum* plant, and then planted into 10 cm diameter pots using standard potting media and cultivation practices (e.g. Hamrick, D., 2003). After one month, the grafted plants were planted into larger pots and the *Argyranthemum* plant was cut away from the aneu-triploid hybrid with a scalpal. After a further two months, the grafted plants were tested for CSVd and CVB infection. All grafted plants tested positive for both CSVd and CVB.

To compare the morphology of infected and uninfected aneu-triploid hybrids an experiment was performed by propagating and growing several accessions using standard growing procedures. Observations were made during and at the compilation of the growing trial. The results are shown in Table 10.

TABLE 9

Aneu-tetraploid *Argyranthemum* × aneu-triploid $F_1$ hybrid crossing

| Female parent | Female pedigree | Male parent | Male pedigree | Capitula pollinated | Embryos rescued | Plants produced |
|---|---|---|---|---|---|---|
| 09-2 | Aneu-tetraploid *Argyranthemum* | 09-78 | 09-2 × 08-80 (*I. versicolor*) | 3 | 6 | 1 |
| 09-5 | Aneu-tetraploid *Argyranthemum* | 09-78 | 09-2 × 08-80 (*I. versicolor*) | 3 | 0 | 0 |
| 09-6 | Aneu-tetraploid *Argyranthemum* | 09-78 | 09-2 × 08-80 (*I. versicolor*) | 3 | 0 | 0 |
| 09-12 | Aneu-tetraploid *Argyranthemum* | 09-78 | 09-2 × 08-80 (*I. versicolor*) | 3 | 1 | 1 |
| 08-119 | Aneu-tetraploid *Argyranthemum* | 09-78 | 09-2 × 08-80 (*I. versicolor*) | 3 | 0 | 0 |
| 09-20 | Aneu-tetraploid *Argyranthemum* | 09-79 | 09-2 × 08-80 (*I. versicolor*) | 3 | 0 | 0 |

TABLE 10

Morphological comparison of several CSVd and CVB infected accessions with uninfected control plants.

| Accession No. | Pedigree | Morphology of CSVd and CVB infected plants compared to uninfected (control) plants |
|---|---|---|
| 09-75 | Aneu-tetraploid *Argyranthemum* × *Ismelia versicolor* | More compact growth, smaller foliage size, slightly earlier flowering |
| 09-81 | Aneu-tetraploid *Argyranthemum* × *Ismelia versicolor* | Flower petals more rounded and overlapping, more vigorous growth, larger foliage size |
| 09-98 | Aneu-tetraploid *Argyranthemum* × *Ismelia versicolor* | Foliage colour different, lime green, more compact growth, more branches, similar flowering time |
| 09-99 | Aneu-tetraploid *Argyranthemum* × *Ismelia versicolor* | Deeper yellow flower colour, more compact growth |
| 09-103 | Aneu-tetraploid *Argyranthemum* × *Ismelia versicolor* | More compact growth, similar flowering time |
| 09-145 | Aneu-tetraploid *Argyranthemum* × *Ismelia versicolor* | Slightly more compact growth, different coloured foliage (lime colour), |
| 09-160 | Aneu-tetraploid *Argyranthemum* × *Ismelia versicolor* | Flower colour faded, more compact growth, earlier flowering |
| 09-162 | Aneu-tetraploid *Argyranthemum* × *Ismelia versicolor* | Flower petals became striped, more compact growth, similar flowering time |
| 09-164 | Aneu-tetraploid *Argyranthemum* × *Ismelia versicolor* | Flower petals became striped, similar flowering time and habit |
| 10-2 | Aneu-tetraploid *Argyranthemum* × *Ismelia versicolor* | More compact growth, larger flower size |
| 10-3 | Aneu-tetraploid *Argyranthemum* × *Ismelia versicolor* | More compact growth, slightly darker yellow flower colour |
| 10-130 | Aneu-tetraploid *Argyranthemum* × *Glebionis coronaria* | More compact growth, increased branching, higher flower number |
| 11-33 | Aneu-tetraploid *Argyranthemum* × *Glebionis coronaria* | Indistinguishable from control |
| 11-36 | Aneu-tetraploid *Argyranthemum* × *Glebionis coronaria* | More compact growth, earlier flowering |
| 11-4 | Aneu-tetraploid *Argyranthemum* × *Glebionis coronaria* | More compact growth, increased branching, higher flower number, earlier flowering, shorter peduncle length |
| 11-55 | Aneu-tetraploid *Argyranthemum* × *Glebionis coronaria* | More compact growth, earlier flowering |
| 11-61 | Aneu-tetraploid *Argyranthemum* × *Glebionis coronaria* | More compact growth |

As shown in Table 10, the results demonstrate that aneu-triploid intergeneric hybrids infected with CSVd and CVB can exhibit changed morphology in such characteristics as flower colour, habit and earliness to flower and many of these changes are beneficial to commercial production.

While a number of exemplary aspects and embodiments have been discussed above, those of skill in the art will recognize certain modifications, permutations, additions, and sub-combinations thereof. It is therefore intended that the following appended claims and claims hereafter introduced are interpreted to include all such modifications, permutations, additions, and sub-combinations as are within their true spirit and scope.

The use of the terms "a," "an," and "the," and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

What is claimed is:

1. An intergeneric hybrid plant produced from a cross between an aneu-tetraploid *Argyranthemum* plant as a male parent crossed with a female parent plant selected from the group consisting of *Ismelia versicolor* and *Glebionis* sp.

2. A plant part of the intergeneric hybrid plant of claim 1.

3. The plant part of claim 2, wherein said plant part is selected from the group consisting of protoplasts, leaves, stems, roots, root tips, anthers, pistils, seed, embryo, pollen, ovules, cotyledon, hypocotyl, capitulum, ray floret, disc floret, shoot, tissue, petiole, cells, and meristematic cells.

4. An intergeneric hybrid plant or plant part thereof clonally propagated from the plant of claim 1.

5. A method of producing an intergeneric hybrid plant comprising:

a. crossing an aneu-tetraploid *Argyranthemum* plant as a male parent with a plant selected from the group consisting of *Ismelia versicolor* and *Glebionis* sp. as a female parent;

b. producing an embryo from said cross;

c. using embryo rescue on said embryo; and d. obtaining an intergeneric hybrid plant grown from said embryo.

6. The method of claim 5, wherein the crossing comprises collecting pollen from said male parent and pollinating a flower on said female parent with this pollen, and wherein the embryo resulting from said pollination is rescued in tissue culture.

7. An intergeneric hybrid plant or part thereof produced by the method of claim 5.

8. An intergeneric hybrid plant or part thereof produced by the method of claim 6.

9. A method of producing an intergeneric hybrid plant comprising the steps of:

a. obtaining a cutting of an intergeneric hybrid plant produced from the cross of an aneu-tetraploid *Argyranthemum* plant as a male parent and a plant selected from the group consisting of *Ismelia versicolor* and *Glebionis* sp. as a female parent; and b. growing said cutting to obtain an intergeneric hybrid plant.

10. The method of claim 9, further comprising the step of applying a plant hormone composition to the base of said cutting to induce the formation of roots.

11. An intergeneric hybrid plant or part thereof produced by the method of claim 9.

12. The method of claim 5, further comprising the step of producing the aneu-tetraploid *Argyranthemum* plant by increasing the chromosome number of an *Argyranthemum* plant prior to step a.

13. The method of claim 12, wherein the increasing of the chromosome number of the *Argyranthemum* plant to produce the aneu-tetraploid comprises the steps of:

a. growing an *Argyranthemum* plant;

b. applying an anti-mitotic agent to said plant;

c. forcing shoots to emerge from said plant;

d. selecting aneu-tetraploid shoots;

e. assessing the chromosome complement of said shoots;

f. growing said shoots to produce an aneu-tetraploid *Argyranthemum* plant; and g. checking chromosomal stability of said aneu-tetraploid *Argyranthemum* plant.

14. The intergeneric hybrid plant of claim 1, wherein said hybrid plant has a chromosome number of 14, 15, 16, 18, 23, 24, 25 or 27.

15. A method of producing an intergeneric hybrid plant comprising:

a. crossing an aneu-tetraploid *Argyranthemum* plant as a female parent with a hybrid male parent derived from intercrossing plants from the group *I. versicolor* and *Glebionis* sp.;

b. producing an embryo from said cross;

c. using embryo rescue on said embryo; and d. obtaining an intergeneric hybrid plant grown from said embryo.

16. An intergeneric hybrid plant or part thereof produced by the method of claim 15.

17. The method of claim 15, wherein said male parent is a hybrid derived from an intergeneric cross of *Ismelia versicolor* and *Glebionis segetum*.

18. The method of claim 15, wherein said male parent is a hybrid derived from an intergeneric cross of *Ismelia versicolor* and *Glebionis coronaria*.

19. The method of claim 15, wherein said male parent is a hybrid derived from an interspecific cross of *Glebionis segetum* and *Glebionis coronaria*.

20. The intergeneric hybrid plant of claim 1, wherein said plant is infected with *Chrysanthemum* Stunt Viroid (CSVd) and *Chrysanthemum* Virus B (CVB).

21. The intergeneric hybrid plant of claim 16, wherein said plant is infected with *Chrysanthemum* Stunt Viroid (CSVd) and *Chrysanthemum* Virus B (CVB).

22. The method of claim 5, wherein said aneu-tetraploid *Argyranthemum* plant has a chromosome number of 32, 33, 34, 35, 37, or 38.

* * * * *